United States Patent
Launay et al.

(10) Patent No.: US 12,037,408 B2
(45) Date of Patent: Jul. 16, 2024

(54) METHOD OF TREATING A TUMOR USING ANTI-TfR ANTIBODIES

(71) Applicant: INATHERYS, Evry (FR)

(72) Inventors: Pierre Launay, Rueil Malmaison (FR); Coralie Belanger, Paris (FR); Hervé Souchet, Paris (FR)

(73) Assignee: INATHERYS, Evry (FR)

( * ) Notice: Subject to any disclaimer, the term of this patent is extended or adjusted under 35 U.S.C. 154(b) by 92 days.

(21) Appl. No.: 17/546,208

(22) Filed: Dec. 9, 2021

(65) Prior Publication Data

US 2022/0119543 A1    Apr. 21, 2022

Related U.S. Application Data

(62) Division of application No. 15/746,590, filed as application No. PCT/EP2016/067465 on Jul. 21, 2016, now Pat. No. 11,230,605.

(30) Foreign Application Priority Data

Jul. 22, 2015  (EP) ...................... 15306192

(51) Int. Cl.
*A61K 39/395* (2006.01)
*C07K 16/28* (2006.01)

(52) U.S. Cl.
CPC ...... *C07K 16/2881* (2013.01); *C07K 2317/24* (2013.01); *C07K 2317/51* (2013.01); *C07K 2317/515* (2013.01); *C07K 2317/565* (2013.01); *C07K 2317/73* (2013.01); *C07K 2317/732* (2013.01); *C07K 2317/92* (2013.01)

(58) Field of Classification Search
None
See application file for complete search history.

(56) References Cited

U.S. PATENT DOCUMENTS

2021/0138083 A1* 5/2021 Launay ............... C07K 16/2881

FOREIGN PATENT DOCUMENTS

WO    WO-2005111082 A1 * 11/2005 ......... C07K 16/2881

OTHER PUBLICATIONS

Candelaria et al., Antibodies Targeting the Transferrin Receptor 1 (TfR1) as Direct Anti-cancer Agents, Front. Immunol. 12:607692. doi: 10.3389/fimmu.2021.607692, 21 pages, 2021.*
Koenig et al., Mutational landscape of antibody variable domains reveals a switch modulating the interdomain conformational dynamics and antigen binding, Proc. Natl. Acad. Sci. USA, 114(4):E486-495, Jan. 2017.*
MacCallum et al., Antibody-antigen interactions: Contact analysis and binding site topography, J. Mol. Biol 262:732, 1996.*
Taetle et al., Role of transferrin, Fe, and transferrin receptors in myeloid leukemia cell growth. Studies with an antitransferrin receptor monoclonal antibody, J Clin Invest. 75(3):1061-1067, doi.org/10.1172/JCI111768, 1985.*

* cited by examiner

*Primary Examiner* — Claire Kaufman
(74) *Attorney, Agent, or Firm* — WC&F IP

(57) ABSTRACT

The present invention relates to humanized antibodies that specifically bind to human transferrin receptor and their use in treating cancer and inflammatory disorders.

3 Claims, 6 Drawing Sheets

Specification includes a Sequence Listing.

| | | | | |
|---|---|---|---|---|
| sequence A24 VL | 1 | LL S AS L - - - - - - - - MS G   I M   K V | 32 | SEQ ID NO: 24 |
| Seq. INA01 VL6 | 1 | | 40 | SEQ ID NO: 25 |
| Seq. INA01 VL5 | 1 | | 40 | SEQ ID NO: 26 |
| Seq. INA01 VL4 | 1 | | 40 | SEQ ID NO: 27 |

M S V P T Q V L G L L L L W L T D A R C Q I V L T Q S P A T L S . S P G E R A T

| | | | | |
|---|---|---|---|---|
| sequence A24 VL | 33 | T       T  K W         L | 72 | SEQ ID NO: 24 |
| Seq. INA01 VL6 | 41 | | 80 | SEQ ID NO: 25 |
| Seq. INA01 VL5 | 41 | | 80 | SEQ ID NO: 26 |
| Seq. INA01 VL4 | 41 | R A T   A | 80 | SEQ ID NO: 27 |

L S C S A S S S V N Y M H W F Q Q K P G Q S P R L L I Y S T S N   A S G V P A R

| | | | | |
|---|---|---|---|---|
| sequence A24 VL | 73 | S   M A A T         A | 112 | SEQ ID NO: 24 |
| Seq. INA01 VL6 | 81 | | 120 | SEQ ID NO: 25 |
| Seq. INA01 VL5 | 81 | F        Q | 120 | SEQ ID NO: 26 |
| Seq. INA01 VL4 | 81 | S     F        Q | 120 | SEQ ID NO: 27 |

F S G S G S G T S Y T L T I S R L E P E D   A V Y Y C Q Q R S S Y P L T F G   G

| | | | | |
|---|---|---|---|---|
| sequence A24 VL | 113 |   I   R | 119 | SEQ ID NO: 24 |
| Seq. INA01 VL6 | 121 | | 160 | SEQ ID NO: 25 |
| Seq. INA01 VL5 | 121 |  I | 160 | SEQ ID NO: 26 |
| Seq. INA01 VL4 | 121 |  I | 160 | SEQ ID NO: 27 |

| sequence A24 VH | 1 | MAAAQSAQA...ETTS | 30 | SEQ ID NO: 28 |
| Seq. INA01 VH5 | 1 | | 40 | SEQ ID NO: 29 |
| Seq. INA01 VH4 | 1 | | 40 | SEQ ID NO: 30 |

MEWSWVFLFFLSVTTGVHSQVQLVQSGPELKKPGASVKVS

| sequence A24 VH | 31 | | 70 | SEQ ID NO: 28 |
| Seq. INA01 VH5 | 41 | | 80 | SEQ ID NO: 29 |
| Seq. INA01 VH4 | 41 | | 80 | SEQ ID NO: 30 |

CKASGYTFTNQGMNWVKQAPGKGLKWMGWINTYTGEPINA

| sequence A24 VH | 71 | ...A......N...M.T... | 110 | SEQ ID NO: 28 |
| Seq. INA01 VH5 | 81 | | 120 | SEQ ID NO: 29 |
| Seq. INA01 VH4 | 81 | ...D......S..A... | 120 | SEQ ID NO: 30 |

DDFKGRFVISLETSASTAYLQISNLKNEDTAVYFCVREGW

| sequence A24 VH | 111 | | 126 | SEQ ID NO: 28 |
| Seq. INA01 VH5 | 121 | | 160 | SEQ ID NO: 29 |
| Seq. INA01 VH4 | 121 | | 160 | SEQ ID NO: 30 |

DSMDYWGQGTSVTVSSASTKGPSVFPLAPCSRSTSESTAA

Figure 5b

SEQUENCE LISTING

```
<160> NUMBER OF SEQ ID NOS: 31

<210> SEQ ID NO 1
<211> LENGTH: 7
<212> TYPE: PRT
<213> ORGANISM: Homo sapiens

<400> SEQUENCE: 1

Gly Tyr Thr Phe Thr Asn Gln
1               5

<210> SEQ ID NO 2
<211> LENGTH: 6
<212> TYPE: PRT
<213> ORGANISM: Homo sapiens

<400> SEQUENCE: 2

Asn Thr Tyr Thr Gly Glu
1               5

<210> SEQ ID NO 3
<211> LENGTH: 8
<212> TYPE: PRT
<213> ORGANISM: Homo sapiens

<400> SEQUENCE: 3

Glu Gly Trp Asp Ser Met Asp Tyr
1               5

<210> SEQ ID NO 4
<211> LENGTH: 10
<212> TYPE: PRT
```

-continued

<213> ORGANISM: Homo sapiens

<400> SEQUENCE: 4

Ser Ala Ser Ser Ser Val Asn Tyr Met His
1               5                   10

<210> SEQ ID NO 5
<211> LENGTH: 7
<212> TYPE: PRT
<213> ORGANISM: Homo sapiens

<400> SEQUENCE: 5

Ser Thr Ser Asn Arg Ala Thr
1               5

<210> SEQ ID NO 6
<211> LENGTH: 9
<212> TYPE: PRT
<213> ORGANISM: Homo sapiens

<400> SEQUENCE: 6

Gln Gln Arg Ser Ser Tyr Pro Leu Thr
1               5

<210> SEQ ID NO 7
<211> LENGTH: 7
<212> TYPE: PRT
<213> ORGANISM: Homo sapiens

<400> SEQUENCE: 7

Ser Thr Ser Asn Leu Ala Ser
1               5

<210> SEQ ID NO 8
<211> LENGTH: 7
<212> TYPE: PRT
<213> ORGANISM: Homo sapiens

<400> SEQUENCE: 8

Ser Thr Ser Asn Arg Ala Ser
1               5

<210> SEQ ID NO 9
<211> LENGTH: 117
<212> TYPE: PRT
<213> ORGANISM: Homo sapiens

<400> SEQUENCE: 9

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Gln
                20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Ile Asn Ala Asp Asp Phe
        50                  55                  60

Lys Gly Arg Phe Ala Ile Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Val Arg Glu Gly Trp Asp Ser Met Asp Tyr Trp Gly Gln Gly Thr Ser
                100                 105                 110

```
Val Thr Val Ser Ser
            115

<210> SEQ ID NO 10
<211> LENGTH: 107
<212> TYPE: PRT
<213> ORGANISM: Homo sapiens

<400> SEQUENCE: 10

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Asn Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys Arg
            100                 105

<210> SEQ ID NO 11
<211> LENGTH: 117
<212> TYPE: PRT
<213> ORGANISM: Homo sapiens

<400> SEQUENCE: 11

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Gln
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Ile Asn Ala Asp Asp Phe
    50                  55                  60

Lys Gly Arg Phe Val Ile Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Val Arg Glu Gly Trp Asp Ser Met Asp Tyr Trp Gly Gln Gly Thr Ser
            100                 105                 110

Val Thr Val Ser Ser
            115

<210> SEQ ID NO 12
<211> LENGTH: 136
<212> TYPE: PRT
<213> ORGANISM: Homo sapiens

<400> SEQUENCE: 12

Met Glu Trp Ser Trp Val Phe Leu Phe Phe Leu Ser Val Thr Thr Gly
1               5                   10                  15

Val His Ser Gln Val Gln Leu Val Gln Ser Gly Pro Glu Leu Lys Lys
            20                  25                  30
```

```
Pro Gly Ala Ser Val Lys Val Ser Cys Lys Ala Ser Gly Tyr Thr Phe
            35                  40                  45

Thr Asn Gln Gly Met Asn Trp Val Lys Gln Ala Pro Gly Lys Gly Leu
 50                  55                  60

Lys Trp Met Gly Trp Ile Asn Thr Tyr Thr Gly Glu Pro Ile Asn Ala
 65                  70                  75                  80

Asp Asp Phe Lys Gly Arg Phe Val Ile Ser Leu Glu Thr Ser Ala Ser
                 85                  90                  95

Thr Ala Tyr Leu Gln Ile Ser Asn Leu Lys Asn Glu Asp Thr Ala Val
                100                 105                 110

Tyr Phe Cys Val Arg Glu Gly Trp Asp Ser Met Asp Tyr Trp Gly Gln
            115                 120                 125

Gly Thr Ser Val Thr Val Ser Ser
        130                 135

<210> SEQ ID NO 13
<211> LENGTH: 107
<212> TYPE: PRT
<213> ORGANISM: Homo sapiens

<400> SEQUENCE: 13

Gln Ile Val Leu Thr Gln Ser Pro Ala Thr Leu Ser Val Ser Pro Gly
 1               5                  10                  15

Glu Arg Ala Thr Leu Ser Cys Ser Ala Ser Ser Val Asn Tyr Met
            20                  25                  30

His Trp Phe Gln Gln Lys Pro Gly Gln Ser Pro Arg Leu Leu Ile Tyr
            35                  40                  45

Ser Thr Ser Asn Arg Ala Thr Gly Ile Pro Ala Arg Phe Ser Gly Ser
 50                  55                  60

Gly Ser Gly Thr Ser Tyr Thr Leu Thr Ile Ser Ser Leu Glu Pro Glu
 65                  70                  75                  80

Asp Phe Ala Val Tyr Tyr Cys Gln Gln Arg Ser Ser Tyr Pro Leu Thr
                 85                  90                  95

Phe Gly Gln Gly Thr Lys Leu Glu Ile Lys Arg
                100                 105

<210> SEQ ID NO 14
<211> LENGTH: 107
<212> TYPE: PRT
<213> ORGANISM: Homo sapiens

<400> SEQUENCE: 14

Gln Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Val Asn Tyr Met
            20                  25                  30

His Trp Phe Gln Gln Lys Pro Gly Gln Ser Pro Arg Leu Leu Ile Tyr
            35                  40                  45

Ser Thr Ser Asn Arg Ala Ser Gly Val Pro Ala Arg Phe Ser Gly Ser
 50                  55                  60

Gly Ser Gly Thr Ser Tyr Thr Leu Thr Ile Ser Arg Leu Glu Pro Glu
 65                  70                  75                  80

Asp Phe Ala Val Tyr Tyr Cys Gln Gln Arg Ser Ser Tyr Pro Leu Thr
                 85                  90                  95

Phe Gly Gln Gly Thr Lys Leu Glu Ile Lys Arg
                100                 105
```

<210> SEQ ID NO 15
<211> LENGTH: 107
<212> TYPE: PRT
<213> ORGANISM: Homo sapiens

<400> SEQUENCE: 15

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Asn Tyr Met
            20                  25                  30

His Trp Phe Gln Gln Lys Pro Gly Gln Ser Pro Arg Leu Leu Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Thr Leu Thr Ile Ser Arg Leu Glu Pro Glu
65                  70                  75                  80

Asp Ala Ala Val Tyr Tyr Cys Gln Gln Arg Ser Ser Tyr Pro Leu Thr
                85                  90                  95

Phe Gly Ala Gly Thr Lys Leu Glu Leu Lys Arg
            100                 105

<210> SEQ ID NO 16
<211> LENGTH: 760
<212> TYPE: PRT
<213> ORGANISM: Homo sapiens

<400> SEQUENCE: 16

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

```
Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
            245                 250                 255

Val Arg Ala Gly Lys Ile Thr Phe Ala Glu Lys Val Ala Asn Ala Glu
        260                 265                 270

Ser Leu Asn Ala Ile Gly Val Leu Ile Tyr Met Asp Gln Thr Lys Phe
    275                 280                 285

Pro Ile Val Asn Ala Glu Leu Ser Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
    355                 360                 365

Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
        420                 425                 430

Phe Ser Asp Met Val Leu Lys Asp Gly Phe Gln Pro Ser Arg Ser Ile
    435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
    515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
```

```
                         645                 650                 655
Thr Thr Asp Phe Gly Asn Ala Glu Lys Thr Asp Arg Phe Val Met Lys
                    660                 665                 670

Lys Leu Asn Asp Arg Val Met Arg Val Glu Tyr His Phe Leu Ser Pro
                675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                    725                 730                 735

Leu Ala Thr Trp Thr Ile Gln Gly Ala Ala Asn Ala Leu Ser Gly Asp
                740                 745                 750

Val Trp Asp Ile Asp Asn Glu Phe
            755                 760

<210> SEQ ID NO 17
<211> LENGTH: 233
<212> TYPE: PRT
<213> ORGANISM: Homo sapiens

<400> SEQUENCE: 17

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Thr Leu Ser
                20                  25                  30

Val Ser Pro Gly Glu Arg Ala Thr Leu Ser Cys Ser Ala Ser Ser Ser
            35                  40                  45

Val Asn Tyr Met His Trp Phe Gln Gln Lys Pro Gly Gln Ser Pro Arg
        50                  55                  60

Leu Leu Ile Tyr Ser Thr Ser Asn Arg Ala Thr Gly Ile Pro Ala Arg
65                  70                  75                  80

Phe Ser Gly Ser Gly Ser Gly Thr Ser Tyr Thr Leu Thr Ile Ser Ser
                85                  90                  95

Leu Glu Pro Glu Asp Phe Ala Val Tyr Tyr Cys Gln Gln Arg Ser Ser
            100                 105                 110

Tyr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 18
<211> LENGTH: 462
```

<212> TYPE: PRT
<213> ORGANISM: Homo sapiens

<400> SEQUENCE: 18

```
Met Glu Trp Ser Trp Val Phe Leu Phe Phe Leu Ser Val Thr Thr Gly
1               5                   10                  15

Val His Ser Gln Val Gln Leu Val Gln Ser Gly Pro Glu Leu Lys Lys
            20                  25                  30

Pro Gly Ala Ser Val Lys Val Ser Cys Lys Ala Ser Gly Tyr Thr Phe
        35                  40                  45

Thr Asn Gln Gly Met Asn Trp Val Lys Gln Ala Pro Gly Lys Gly Leu
    50                  55                  60

Lys Trp Met Gly Trp Ile Asn Thr Tyr Thr Gly Glu Pro Ile Asn Ala
65                  70                  75                  80

Asp Asp Phe Lys Gly Arg Phe Val Ile Ser Leu Asp Thr Ser Ala Ser
                85                  90                  95

Thr Ala Tyr Leu Gln Ile Ser Ser Leu Lys Ala Glu Asp Thr Ala Val
            100                 105                 110

Tyr Phe Cys Val Arg Glu Gly Trp Asp Ser Met Asp Tyr Trp Gly Gln
        115                 120                 125

Gly Thr Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400
```

```
Gly Gln Pro Glu Asn Asn Tyr Lys Thr Thr Pro Pro Val Leu Asp Ser
            405                 410                 415

Asp Gly Ser Phe Phe Leu Tyr Ser Arg Leu Thr Val Asp Lys Ser Arg
        420                 425                 430

Trp Gln Glu Gly Asn Val Phe Ser Cys Ser Val Met His Glu Ala Leu
    435                 440                 445

His Asn His Tyr Thr Gln Lys Ser Leu Ser Leu Ser Leu Gly
    450                 455                 460

<210> SEQ ID NO 19
<211> LENGTH: 724
<212> TYPE: DNA
<213> ORGANISM: Homo sapiens

<400> SEQUENCE: 19
aagcttgccg ccaccatgtc cgtgcctacc caggtgctgg gactgctgct gctgtggctg      60
accgatgcca ggtgccagat cgtgctgacc cagtctcctg ccaccctgtc tgtgtctccc     120
ggcgagagag ctaccctgtc ctgctccgcc tcctcctccg tgaactacat gcactggttc     180
cagcagaagc ccggccagtc ccccagactg ctgatctact ccacctccaa ccgggccacc     240
ggcatccctg ccagattttc cggctctggc tccggcacct cctataccct gaccatctcc     300
agcctggaac ccgaggactt cgccgtgtac tactgccagc agcggtcctc ctacccctg      360 acctttggcc agggcaccaa gctggaaatc aagcgtacgg tggccgctcc cagcgtgttc     420
atcttccccc caagcgacga gcagctgaag agcggcaccg ccagcgtggt gtgtctgctg     480
aacaacttct accccaggga ggccaaggtg cagtggaagg tggacaacgc cctgcagagc     540
ggcaacagcc aggagagcgt caccgagcag gacagcaagg actccaccta cagcctgagc     600
agcaccctga ccctgagcaa ggccgactac gagaagcaca aggtgtacgc ctgtgaggtg     660
acccaccagg gcctgtccag ccccgtgacc aagagcttca caggggcga gtgctgatga     720 attc                                                                 724

<210> SEQ ID NO 20
<211> LENGTH: 1411
<212> TYPE: DNA
<213> ORGANISM: Homo sapiens

<400> SEQUENCE: 20
aagcttgccg ccaccatgga atggtcctgg gtgttcctgt tcttcctgtc cgtgaccacc      60
ggcgtgcact cccaggtgca gctggtgcag tctggccccg agctgaagaa acctggcgcc     120
tccgtgaagg tgtcctgcaa ggcttccggc tacacctta caaaccaggg catgaactgg     180
gtcaagcagg cccctggcaa gggcctgaag tggatgggct ggatcaacac ctacaccggc     240
gagcccatca cgccgacga cttcaagggc agattcgtga tctccctgga cacctccgcc     300
tccaccgcct acctgcagat cagctctctg aaggccgagg ataccgccgt gtacttctgc     360
gtgcgggaag ctgggactc catggactat tggggccagg gcacctccgt gaccgtgtct     420
agcgcttcta caagggccc aagcgtgttc cccctggccc cctgctccag aagcaccagc     480
gagagcacag ccgccctggg ctgcctggtg aaggactact ccccgagcc cgtgaccgtg     540 tcctggaaca gcggagccct gaccagcggc gtgcacacct cccgccgt gctgcagagc     600 agcggcctgt acagcctgag cagcgtggtg accgtgccca gcagcagcct gggcaccaag     660
acctacacct gtaacgtgga ccacaagccc agcaacacca aggtggacaa gagggtggag     720
```

-continued

```
agcaagtacg gcccaccctg ccccccctgc ccagccccg  agttcctggg cggacccagc      780
gtgttcctgt tccccccaa  gcccaaggac accctgatga tcagcagaac ccccgaggtg      840
acctgtgtgg tggtggacgt gtcccaggag daccccgagg tccagttcaa ctggtacgtg      900
gacggcgtgg aggtgcacaa cgccaagacc aagcccagag aggagcagtt taacagcacc      960
taccgggtgg tgtccgtgct gaccgtgctg caccaggact ggctgaacgg caaagagtac     1020
aagtgtaagg tctccaacaa gggcctgcca agcagcatcg aaaagaccat cagcaaggcc     1080
aagggccagc tagagagcc  ccaggtctac accctgccac ccagccaaga ggagatgacc     1140
aagaaccagg tgtccctgac ctgtctggtg aagggcttct acccaagcga catcgccgtg     1200
gagtgggaga gcaacggcca gcccgagaac aactacaaga ccacccccc  agtgctggac     1260 agcgacggca gcttcttcct gtacagcagg ctgaccgtgg acaagtccag atggcaggag     1320
ggcaacgtct ttagctgctc cgtgatgcac gaggccctgc acaaccacta cacccagaag     1380
agcctgagcc tgtccctggg ctgatgaatt c                                    1411
```

<210> SEQ ID NO 21
<211> LENGTH: 9
<212> TYPE: PRT
<213> ORGANISM: Homo sapiens

<400> SEQUENCE: 21

Ile Tyr Ser Thr Ser Asn Arg Ala Thr
1               5

<210> SEQ ID NO 22
<211> LENGTH: 9
<212> TYPE: PRT
<213> ORGANISM: Homo sapiens

<400> SEQUENCE: 22

Ile Tyr Ser Thr Ser Asn Arg Ala Ser
1               5

<210> SEQ ID NO 23
<211> LENGTH: 9
<212> TYPE: PRT
<213> ORGANISM: Homo sapiens

<400> SEQUENCE: 23

Ile Tyr Ser Thr Ser Asn Leu Ala Ser
1               5

<210> SEQ ID NO 24
<211> LENGTH: 121
<212> TYPE: PRT
<213> ORGANISM: Homo sapiens

<400> SEQUENCE: 24

Leu Leu Ile Ser Ala Ser Val Ile Met Ser Arg Gly Gln Ile Val Leu
1               5                   10                  15

Thr Gln Ser Pro Ala Ile Met Ser Ala Ser Pro Gly Glu Lys Val Thr
                20                  25                  30

Ser Pro Ile Thr Cys Ser Ala Ser Ser Val Asn Tyr Met His Trp
            35                  40                  45

Phe Gln Gln Lys Pro Gly Thr Ser Pro Lys Leu Trp Ile Tyr Ser Thr
        50                  55                  60

Ser Asn Leu Ala Ser Gly Val Pro Ala Arg Phe Ser Cys Ser Gly Ser
65                  70                  75                  80

Gly Thr Ser Tyr Ser Leu Thr Ile Ser Arg Met Glu Ala Glu Asp Ala
            85                  90                  95

Ala Thr Tyr Tyr Cys Gln Gln Arg Ser Ser Tyr Pro Leu Thr Phe Gly
            100                 105                 110

Ala Gly Thr Lys Leu Glu Leu Lys Arg
        115                 120

<210> SEQ ID NO 25
<211> LENGTH: 160
<212> TYPE: PRT
<213> ORGANISM: Homo sapiens

<400> SEQUENCE: 25

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Val Asn Tyr Met His Trp Phe Gln Gln Lys Pro Gly Gln Ser Pro Arg
    50                  55                  60

Leu Leu Ile Tyr Ser Thr Ser Asn Leu Ala Ser Gly Val Pro Ala Arg
65                  70                  75                  80

Phe Ser Gly Ser Gly Ser Gly Thr Ser Tyr Thr Leu Thr Ile Ser Arg
                85                  90                  95

Leu Glu Pro Glu Asp Ala Ala Val Tyr Tyr Cys Gln Gln Arg Ser Ser
            100                 105                 110

Tyr Pro Leu Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

<210> SEQ ID NO 26
<211> LENGTH: 160
<212> TYPE: PRT
<213> ORGANISM: Homo sapiens

<400> SEQUENCE: 26

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Val Asn Tyr Met His Trp Phe Gln Gln Lys Pro Gly Gln Ser Pro Arg
    50                  55                  60

Leu Leu Ile Tyr Ser Thr Ser Asn Arg Ala Ser Gly Val Pro Ala Arg
65                  70                  75                  80

Phe Ser Gly Ser Gly Ser Gly Thr Ser Tyr Thr Leu Thr Ile Ser Arg
                85                  90                  95

Leu Glu Pro Glu Asp Phe Ala Val Tyr Tyr Cys Gln Gln Arg Ser Ser
            100                 105                 110

Tyr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

<210> SEQ ID NO 27
<211> LENGTH: 160
<212> TYPE: PRT
<213> ORGANISM: Homo sapiens

<400> SEQUENCE: 27

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Thr Leu Ser
            20                  25                  30

Val Ser Pro Gly Glu Arg Ala Thr Leu Ser Cys Ser Ala Ser Ser Ser
        35                  40                  45

Val Asn Tyr Met His Trp Phe Gln Gln Lys Pro Gly Gln Ser Pro Arg
    50                  55                  60

Leu Leu Ile Tyr Ser Thr Ser Asn Arg Ala Thr Gly Ile Pro Ala Arg
65                  70                  75                  80

Phe Ser Gly Ser Gly Ser Gly Thr Ser Tyr Thr Leu Thr Ile Ser Ser
                85                  90                  95

Leu Glu Pro Glu Asp Phe Ala Val Tyr Tyr Cys Gln Gln Arg Ser Ser
            100                 105                 110

Tyr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

<210> SEQ ID NO 28
<211> LENGTH: 160
<212> TYPE: PRT
<213> ORGANISM: Homo sapiens
<220> FEATURE:
<221> NAME/KEY: MISC_FEATURE
<222> LOCATION: (33)..(33)
<223> OTHER INFORMATION: X is A, L or V
<220> FEATURE:
<221> NAME/KEY: MISC_FEATURE
<222> LOCATION: (73)..(73)
<223> OTHER INFORMATION: X is L or R
<220> FEATURE:
<221> NAME/KEY: MISC_FEATURE
<222> LOCATION: (102)..(102)
<223> OTHER INFORMATION: X is A or F
<220> FEATURE:
<221> NAME/KEY: MISC_FEATURE
<222> LOCATION: (119)..(119)
<223> OTHER INFORMATION: X is A or Q
<220> FEATURE:
<221> NAME/KEY: MISC_FEATURE
<222> LOCATION: (125)..(125)
<223> OTHER INFORMATION: X is I or L

<400> SEQUENCE: 28

Met Ser Val Pro Thr Gln Val Leu Gly Leu Leu Leu Leu Trp Leu Thr
1               5                   10                  15

Asp Ala Arg Cys Gln Ile Val Leu Thr Gln Ser Pro Ala Thr Leu Ser
            20                  25                  30

Xaa Ser Pro Gly Glu Arg Ala Thr Leu Ser Cys Ser Ala Ser Ser Ser
         35                  40                  45

Val Asn Tyr Met His Trp Phe Gln Gln Lys Pro Gly Gln Ser Pro Arg
 50                  55                  60

Leu Leu Ile Tyr Ser Thr Ser Asn Xaa Ala Thr Gly Ile Pro Ala Arg
 65                  70                  75                  80

Phe Ser Gly Ser Gly Ser Gly Thr Ser Tyr Thr Leu Thr Ile Ser Ser
                 85                  90                  95

Leu Glu Pro Glu Asp Xaa Ala Val Tyr Tyr Cys Gln Gln Arg Ser Ser
                100                 105                 110

Tyr Pro Leu Thr Phe Gly Xaa Gly Thr Lys Leu Glu Xaa Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

<210> SEQ ID NO 29
<211> LENGTH: 126
<212> TYPE: PRT
<213> ORGANISM: Homo sapiens

<400> SEQUENCE: 29

Met Ala Ala Ala Gln Ser Ala Gln Ala Gln Ile Gln Leu Val Gln Ser
 1               5                  10                  15

Gly Pro Glu Leu Lys Lys Pro Gly Glu Thr Val Lys Ile Ser Cys Lys
                20                  25                  30

Ala Ser Gly Tyr Thr Phe Thr Asn Gln Gly Met Asn Trp Val Lys Gln
             35                  40                  45

Ala Pro Gly Lys Gly Leu Lys Trp Met Gly Trp Ile Asn Thr Tyr Thr
 50                  55                  60

Gly Glu Pro Ile Asn Ala Asp Asp Phe Lys Gly Arg Phe Ala Ile Ser
 65                  70                  75                  80

Leu Glu Thr Ser Ala Ser Thr Ala Tyr Leu Gln Ile Asn Asn Leu Lys
                 85                  90                  95

Asn Glu Asp Met Ala Thr Tyr Phe Cys Val Arg Glu Gly Trp Asp Ser
                100                 105                 110

Met Asp Tyr Trp Gly Gln Gly Thr Ser Val Thr Val Ser Ser
            115                 120                 125

<210> SEQ ID NO 30
<211> LENGTH: 160
<212> TYPE: PRT
<213> ORGANISM: Homo sapiens

<400> SEQUENCE: 30

Met Glu Trp Ser Trp Val Phe Leu Phe Phe Leu Ser Val Thr Thr Gly
 1               5                  10                  15

Val His Ser Gln Val Gln Leu Val Gln Ser Gly Pro Glu Leu Lys Lys
                20                  25                  30

Pro Gly Ala Ser Val Lys Val Ser Cys Lys Ala Ser Gly Tyr Thr Phe
             35                  40                  45

Thr Asn Gln Gly Met Asn Trp Val Lys Gln Ala Pro Gly Lys Gly Leu
 50                  55                  60

Lys Trp Met Gly Trp Ile Asn Thr Tyr Thr Gly Glu Pro Ile Asn Ala
 65                  70                  75                  80

```
Asp Asp Phe Lys Gly Arg Phe Val Ile Ser Leu Glu Thr Ser Ala Ser
                85                  90                  95

Thr Ala Tyr Leu Gln Ile Ser Asn Leu Lys Asn Glu Asp Thr Ala Val
            100                 105                 110

Tyr Phe Cys Val Arg Glu Gly Trp Asp Ser Met Asp Tyr Trp Gly Gln
        115                 120                 125

Gly Thr Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

<210> SEQ ID NO 31
<211> LENGTH: 160
<212> TYPE: PRT
<213> ORGANISM: Homo sapiens

<400> SEQUENCE: 31

Met Glu Trp Ser Trp Val Phe Leu Phe Phe Leu Ser Val Thr Thr Gly
1               5                   10                  15

Val His Ser Gln Val Gln Leu Val Gln Ser Gly Pro Glu Leu Lys Lys
                20                  25                  30

Pro Gly Ala Ser Val Lys Val Ser Cys Lys Ala Ser Gly Tyr Thr Phe
            35                  40                  45

Thr Asn Gln Gly Met Asn Trp Val Lys Gln Ala Pro Gly Lys Gly Leu
        50                  55                  60

Lys Trp Met Gly Trp Ile Asn Thr Tyr Thr Gly Glu Pro Ile Asn Ala
65                  70                  75                  80

Asp Asp Phe Lys Gly Arg Phe Val Ile Ser Leu Asp Thr Ser Ala Ser
                85                  90                  95

Thr Ala Tyr Leu Gln Ile Ser Ser Leu Lys Ala Glu Asp Thr Ala Val
            100                 105                 110

Tyr Phe Cys Val Arg Glu Gly Trp Asp Ser Met Asp Tyr Trp Gly Gln
        115                 120                 125

Gly Thr Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160
```

METHOD OF TREATING A TUMOR USING ANTI-TfR ANTIBODIES

SEQUENCE LISTING

This document incorporates by reference an electronic sequence listing file, which was electronically submitted along with this document. The text file is named 13500081US2_SequenceListing.txt, is 36015 bytes, and was created on Dec. 9, 2021.

FIELD OF THE INVENTION

It is hereafter disclosed antibodies that specifically bind to TfR, the transferrin receptor. Such antibodies are useful in particular in treating proliferative and inflammatory disorders, such as lymphoma or leukaemia. The disclosure more specifically relates to specific humanized anti-TfR antibodies, with equivalent or improved properties as compared to the corresponding parental murine antibody of A24, or its chimeric version with human IgG1 constant region.

BACKGROUND

The transferrin receptor (CD71) (hereafter referred to as "TfR") is a disulfide-linked homodimeric transmembrane glycoprotein consisting of two 760-amino acid monomers of approximately 90 kDa each. TfR plays a crucial role in the regulation of iron uptake and cell growth (Gill et al., N Engl J Med., 332, 1744-1748, 1995—Hermine et al., N Engl J Med., 332, 1749-1751, 1995). When diferric transferrin binds to its cell surface receptor, it is internalized via clathrin-coated pits to acidic vesicles where the iron-transferrin complex is dissociated. After release, the receptor and apo-transferrin recycle back to the cell surface.

TfR is constitutively expressed at the cell plasma membrane of tissues that are constantly renewed, such as precursors of blood cells in the bone marrow, hepatocytes in the liver, keratinocytes in the epidermis and enterocytes in crypts of intestinal epithelium.

Several studies have shown that TfR is expressed more abundantly in malignant tissues than in their healthy counterparts (Gatter et al., J Clin Pathol., 36,539-545, 1983—Faulk et al, Lancet., 2,390-392, 1980—Shindelman et al., Int J Cancer, 27,329-334, 1981). Several authors have reported therapeutic approaches based on this idea using anti-TfR antibodies or transferrin itself conjugated to drugs to kill malignant cells.

It has also been proposed to use anti-TfR antibodies to block the interaction between transferrin and TfR, and consequently preventing iron uptake, leading to iron deprivation and negative regulation of cell growth. However, although many publications describe the preparation of anti-TfR antibodies, there are very few reports of anti-TfR monoclonal antibodies (mAbs) having an antiproliferative activity.

Trowbridge and Lopez (Proc. Natl Acad Sci USA, 79, 1175-1179, 1982) report the properties of a monoclonal antibody, designated 42/6 and typed as IgA (k), that blocks the binding of transferrin to its receptor and is able to inhibit in vitro the growth of an human T leukemic cell line, by blocking the cells in S phase of the cell cycle. The 42/6 antibody and the hybridoma producing it (ATCC HB-8094) are disclosed in U.S. Pat. No. 4,434,156.

Lesley et al. (Mol Cell Biol. 5, 1814-21, 1985) have studied the effects of anti-murine transferrin receptor monoclonal antibodies belonging to either the IgG or the IgM class, on binding of transferrin and on murine lymphoma cell growth in vitro. They observed that the IgM inhibited cell growth but that the IgG did not, although they were able to induce a down-regulation and a degradation of the TfR. However, IgG cross-linked by an anti-immunoglobulin antibody were able to inhibit cell growth. In a subsequent work, the same team (Lesley et al., Exp Cell Res., 182,215-33, 1989) has studied the effects of IgG and IgM monoclonal anti-TfR antibodies and of their mono- and divalent fragments on murine lymphoma cell growth and TfR expression. They report that these effects depend on the degree of crosslinking of transferrin receptors by the antibody, which is a consequence of the antibody valence. Monovalent antibody fragments had no significant effects; divalent antibody fragments induced a down-regulation of cell-surface receptor expression without impairing its internalization and recycling and without impairing cell growth; multivalent IgM induced the accumulation of antibody-complexed receptor on the cell surface, blocking its internalization and resulting in a strong inhibition of cell growth.

It appears from the prior art cited above that the antiproliferative properties of anti-TfR antibodies strongly vary from an antibody to another and that they cannot be predicted on the basis of their ability to block or not transferrin binding to its receptor.

In a previous publication (Moura et al., J Exp Med, 194, 417-425, 2001), the inventors have reported a mouse monoclonal IgG (IgG2kappa), designated A24, that bind to the human TfR.

WO2005/111082 discloses the A24 antibody, a murine antibody able to block T cell proliferation, and which appeared to be more efficient than the previously described mAb 42/6 in inhibiting proliferation of T cells. A24 prevents Tf from binding to TfR in a competitive manner. A24 also reduced TfR expression and impaired TfR recycling. A24 is also able to block the ex vivo proliferation of malignant T cells from both acute and chronic forms of ATL (Moura et al., Blood, 103, 5, 1838-45, 1 Mar. 2004, Callens et al., 2010; J. Exp. Med., Vol 207 No 4, pp 731-750). This antibody has been also described as able to prevent the mantle cell lymphoma tumor development both in vitro and in vivo (Lepelletier et al. Cancer Res 2007; 67:1145-1154; Callens et al. 2008, Leukemia, 22, 42-48).

For administration to human, it is nowadays mandatory to humanize antibodies of murine origin, to avoid immunogenicity reactions. However, when performing the first humanization process of the A24 antibody, the inventors found a loss of binding and apoptotic properties among all the humanized variants. The inventors thus had to design specific variants of A24 in several steps of humanization, which combine maintained functional properties of A24 parental antibody with predicted decrease immunogenicity for human.

SUMMARY

The disclosure thus relates to an isolated anti-TfR antibody or a protein with an antigen-binding portion of an anti-TfR antibody, comprising either,
(a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6;
(b) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:8 and LCDR3 of SEQ ID NO:6;

(c) a variable heavy chain polypeptide comprising VH of SEQ ID NO:11 and a variable light chain polypeptide comprising VL of SEQ ID NO:13;

(d) a variable heavy chain polypeptide comprising VH of SEQ ID NO:11 and a variable light chain polypeptide comprising VL of SEQ ID NO:14;

(e) a variable heavy chain polypeptide comprising VH of SEQ ID NO:11 and a variable light chain polypeptide comprising VL of SEQ ID NO:15;

(f) a variable heavy chain polypeptide comprising VH of SEQ ID NO:12 and a variable light chain polypeptide comprising VL of SEQ ID NO:13;

(g) a variable heavy chain polypeptide comprising VH of SEQ ID NO:12 and a variable light chain polypeptide comprising VL of SEQ ID NO:14;

(h) a variable heavy chain polypeptide comprising VH of SEQ ID NO:12 and a variable light chain polypeptide comprising VL of SEQ ID NO:15;

wherein said anti-TfR antibody or protein specifically binds to the transferrin receptor of SEQ ID NO:16.

In a specific embodiment, said antibody or protein binds to the transferrin receptor with a $K_D$ of 10 nM or less, preferably with a $K_D$ of 1 nM or less.

In another specific embodiment, said antibody or protein induces apoptosis of HL-60 cell line to a level equal or superior to the induction level measured with the corresponding chimeric antibody with parental murine variable regions having VH of SEQ ID NO:9 and VL of SEQ ID NO:10.

Preferably, such anti-TfR antibody according to the present disclosure is a humanized anti-TfR antibody.

In another specific embodiment that may be combined with the previous embodiments, said anti-TfR antibody comprises a human IgG4 isotype constant region, or a mutant or chemically modified constant region, wherein said mutant or chemically modified constant region confers no or decreased ADCC activity to said antibody when compared to a corresponding antibody with wild type IgG1 isotype constant region. Alternatively, said anti-TfR antibody or protein may comprise a human IgG1 isotype constant region, or a mutant or chemically modified constant region, wherein said mutant or chemically modified constant region confers increased ADCC activity of said antibody when compared to a corresponding antibody with wild type IgG1 isotype constant region.

Examples of antibodies according to the invention include the humanized anti-TfR antibody mAb1 to mAb16 as described below, in particular in Table 1.

Also disclosed herein are isolated anti-TfR antibodies or proteins as defined above, for use as a medicament, or in diagnostic, for example, for use in the treatment of a tumor. Said tumor is preferably a hematologic tumor, e.g. a lymphoma or leukaemia.

Alternatively, said isolated anti-TfR antibody or protein may also be used in the treatment of HTLV-1 related diseases, to reduce the viral load in inflammatory disorders associated with HTLV-1 infection, including HAM/TSP, polymyositis, and arthritis.

The disclosure further relates to a pharmaceutical composition comprising an anti-TfR antibody or protein as defined above, in combination with one or more of a pharmaceutically acceptable excipient, diluent or carrier. The pharmaceutical composition may additionally include other active ingredients.

In a specific embodiment, said composition is a lyophilisate formulation, or a pre-filled syringe or pre-filled vial, comprising a therapeutically acceptable amount of an anti-TfR antibody or protein as defined above.

The disclosure also relates to an isolated nucleic acid encoding at least the heavy and/or light chain variable region(s) of the antibody or protein as defined above; a cloning or expression vector comprising one or more of such nucleic acids, or a cloning or expression vector for the recombinant production of an anti-TfR antibody as defined above in a host cell.

In a specific embodiment, the cloning or expression vector comprises either at least one of the following nucleic acids encoding the heavy and light chain polypeptides of any one of the mAb1 to mAb16 as defined in the Examples below.

The present disclosure also relates to a host cell comprising one or more cloning or expression vectors as defined above.

The disclosure further relates to a process for the production of an anti-TfR antibody or a protein as defined above, comprising: (i) culturing the host cell of the disclosure for expression of said antibody or protein by the host cell; optionally (ii) purifying said antibody or protein; and, (iii) recovering said antibody or protein.

LEGENDS OF THE FIGURES

Figure 4:
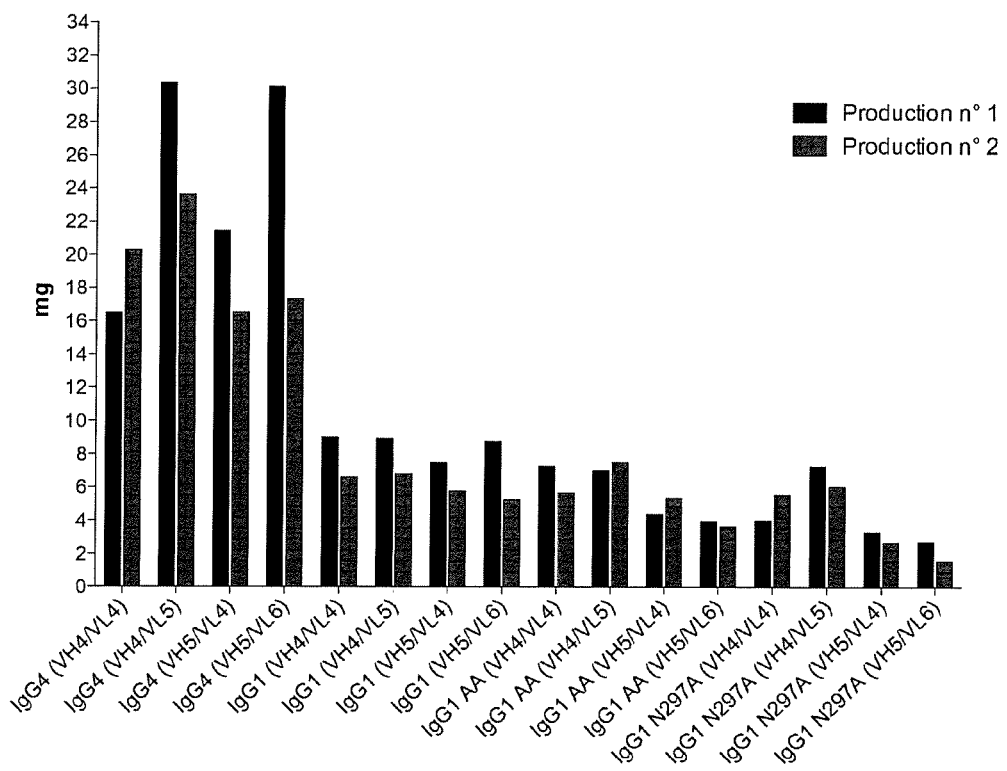

FIG. 4 Productivity yield of mAb1 to mAb16: The amount (mg) of each produced antibody mAb1 to mAb16 is shown based on 2 production batches.

FIG. 5a-b shows the alignment of VL sequences according to the disclosure with the parent A24 VL (FIG. 5a) and the alignment of VH sequences according to the disclosure with the parent A24 VH (FIG. 5b).

DETAILED DESCRIPTION

Definitions

In order that the present disclosure may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term CD71 or transferrin receptor or TfR refers to human TfR as defined in SEQ ID NO: 16, unless otherwise described.

The term "antibody" as referred to herein includes whole antibodies and any antigen binding fragments (i.e., "antigen-binding portion") or single chains thereof.

A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of TfR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a Unibody consisting of a single arm with a modified IgG heavy chain, for example IgG4, at the hinge region, a domain antibody fragment (Ward et al., 1989 Nature 341:544-546), or a nanobody fragment which consists of a VH domain; and an isolated complementarity determining region (CDR), or any fusion proteins comprising such antigen-binding portion.

Furthermore, although the two domains of the Fv fragment, VL and VH, are coded for by separate genes, they can be joined, using recombinant methods, by a synthetic linker that enables them to be made as a single chain protein in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds to TfR is substantially free of antibodies that specifically bind to other antigens than TfR). An isolated antibody that specifically binds to TfR may, however, have cross-reactivity to other antigens, such as TfR molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, "isotype" refers to the antibody class (e.g., IgM, IgE, IgG such as IgG1 or IgG4) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody or a protein that "specifically binds to an antigen", for example that "specifically binds to TfR" is intended to refer to an antibody or protein that binds to said antigen (for example human TfR of SEQ ID NO:16) with a $K_D$ of 100 nM or less, 10 nM or less, 1 nM or less.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. An assay for measuring anti-TfR antibody $K_D$ with the Biacore® system is described in the Examples below.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope. In a specific embodiment, said anti-TfR antibody of the disclosure is a bivalent antibody.

As used herein, the term "HL-60 cell line" refers to the promyelocytic derived by Collins et al. (PNAS 1978, 75:2458-1462) and also described in Gallagher et al (Blood, 1979, 54:713-733), for example available at ATCC® collection under catalog number CCL-240™.

As used herein, the antibody A24 refers to the antibody as disclosed in WO2005/111082.

As used herein, the term "ADCC" or "antibody dependent cell cytotoxicity" activity refers to cell depleting activity. ADCC activity can be measured by ADCC assays commercially available, for example, ADCC Reporter Bioassay as commercialized by Promega under Ref #G7015, and as briefly described in the Examples.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a Chinese Hamster Ovary cell (CHO) or a human cell. The optimized nucleotide sequence is engineered to retain completely or as much as possible the amino acid sequence originally encoded by the starting nucleotide sequence. The amino acid sequences encoded by optimized nucleotide sequences are also referred to as optimized.

As used herein, the percent identity between the two sequences is a function of the number of identical positions shared by the sequences (i. e., % identity=number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

Recombinant Antibodies

Antibodies of the disclosure include the humanized recombinant antibodies mAb1-mAb16, isolated and structurally characterized by their variable heavy and light chain amino acid sequences and human constant isotype as described in the Table 1 below:

TABLE 1

Variable heavy and light chain amino acid sequences of mAb1-mAb16

| Antibody | VH Amino acid sequence | VL Amino acid sequence | Isotype constant region |
|---|---|---|---|
| mAb1 | SEQ ID NO: 11 (VH4) | SEQ ID NO: 13 (VL4) | IgG4 |
| mAb2 | SEQ ID NO: 11 (VH4) | SEQ ID NO: 14 (VL5) | IgG4 |
| mAb3 | SEQ ID NO: 12 (VH5) | SEQ ID NO: 13 (VL4) | IgG4 |
| mAb4 | SEQ ID NO: 12 (VH5) | SEQ ID NO: 15 (VL6) | IgG4 |
| mAb5 | SEQ ID NO: 11 (VH4) | SEQ ID NO: 13 (VL4) | IgG1 |
| mAb6 | SEQ ID NO: 11 (VH4) | SEQ ID NO: 14 (VL5) | IgG1 |
| mAb7 | SEQ ID NO: 12 (VH5) | SEQ ID NO: 13 (VL4) | IgG1 |
| mAb8 | SEQ ID NO: 12 (VH5) | SEQ ID NO: 15 (VL6) | IgG1 |
| mAb9 | SEQ ID NO: 11 (VH4) | SEQ ID NO: 13 (VL4) | IgG1 (AA) |
| mAb10 | SEQ ID NO: 11 (VH4) | SEQ ID NO: 14 (VL5) | IgG1 (AA) |
| mAb11 | SEQ ID NO: 12 (VH5) | SEQ ID NO: 13 (VL4) | IgG1 (AA) |
| mAb12 | SEQ ID NO: 12 (VH5) | SEQ ID NO: 15 (VL6) | IgG1 (AA) |
| mAb13 | SEQ ID NO: 11 (VH4) | SEQ ID NO: 13 (VL4) | IgG1 N297A |
| mAb14 | SEQ ID NO: 11 (VH4) | SEQ ID NO: 14 (VL5) | IgG1 N297A |
| mAb15 | SEQ ID NO: 12 (VH5) | SEQ ID NO: 13 (VL4) | IgG1 N297A |
| mAb16 | SEQ ID NO: 12 (VH5) | SEQ ID NO: 15 (VL6) | IgG1 N297A |

The corresponding amino acid and nucleotide coding sequence of the constant isotype regions of IgG4, IgG1 and their mutant versions IgG1 AA and IgG1 N297A used for generating mAb1 to mAb16 are well-known in the art.

Full length light and heavy chains and corresponding coding sequences of mAb1 is shown in the Table 2 below.

TABLE 2

Full length heavy and light chain DNA coding sequences

| Antibody | Amino acid sequence | DNA coding sequence |
|---|---|---|
| mAb1 | Heavy Chain: SEQ ID NO: 18 Light Chain : SEQ ID NO: 17 | Heavy Chain: SEQ ID NO: 20 Light Chain : SEQ ID NO: 19 |

Examples of the amino acid sequences of the VH CDR1s (also called HCDR1), VH CDR2s (also called HCDR2), VH CDR3s (also called HCDR1), VL CDR1s (also called LCDR1), VL CDR2s (also called LCDR2), VL CDR3s (also called HCDR3) of some antibodies according to the disclosure are shown in Table 3.

In Table 3, the CDR regions of some antibodies of the present disclosure are delineated using the Chothia system (Chothia C, Lesk A M. 1987, J Mol Biol 196, 901-917).

For the ease of reading, the CDR regions are called hereafter HCDR1, HCDR2, HCDR3, LCDR1, LCDR2, LCDR3 respectively.

| Original antibody | HCDR1 | HCDR2 | HCDR3 | LCDR1 | LCDR2 | LCDR3 |
|---|---|---|---|---|---|---|
| A24 | SEQ ID NO: 1 | SEQ ID NO: 2 | SEQ ID NO: 3 | SEQ ID NO: 4 | SEQ ID NO: 7 | SEQ ID NO: 6 |
| mAb1 mAb5 mAb9 mAb13 | SEQ ID NO: 1 | SEQ ID NO: 2 | SEQ ID NO: 3 | SEQ ID NO: 4 | SEQ ID NO: 5 | SEQ ID NO: 6 |
| mAb2 mAb6 mAb10 mAb14 | SEQ ID NO: 1 | SEQ ID NO: 2 | SEQ ID NO: 3 | SEQ ID NO: 4 | SEQ ID NO: 8 | SEQ ID NO: 6 |
| mAb3 mAb7 mAb11 mAb15 | SEQ ID NO: 1 | SEQ ID NO: 2 | SEQ ID NO: 3 | SEQ ID NO: 4 | SEQ ID NO: 5 | SEQ ID NO: 6 |

-continued

| Original antibody | HCDR1 | HCDR2 | HCDR3 | LCDR1 | LCDR2 | LCDR3 |
|---|---|---|---|---|---|---|
| mAb4<br>mAb8<br>mAb12<br>mAb16 | SEQ ID NO: 1 | SEQ ID NO: 2 | SEQ ID NO: 3 | SEQ ID NO: 4 | SEQ ID NO: 7 | SEQ ID NO: 6 |

In one embodiment, an isolated recombinant antibody has: a heavy chain variable region comprising HCDR1 of SEQ ID NO: 1; HCDR2 of SEQ ID NO: 2; HCDR3 of SEQ ID NO: 3; a light chain variable region comprising LCDR1 of SEQ ID NO: 4; LCDR2 of SEQ ID NOs: 5 or 8; and LCDR3 of SEQ ID NOs: 6; wherein said antibody specifically binds to the transferrin receptor of SEQ ID NO:16.

In specific embodiments, the isolated recombinant antibody according to the disclosure comprises either:
  (a) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:5 and LCDR3 of SEQ ID NO:6;
  (b) a variable heavy chain polypeptide comprising HCDR1 of SEQ ID NO:1, HCDR2 of SEQ ID NO:2, HCDR3 of SEQ ID NO:3 and a variable light chain polypeptide comprising LCDR1 of SEQ ID NO:4, LCDR2 of SEQ ID NO:8 and LCDR3 of SEQ ID NO:6;
  (c) a variable heavy chain polypeptide comprising VH of SEQ ID NO:11 and a variable light chain polypeptide VL of SEQ ID NO:13;
  (d) a variable heavy chain polypeptide comprising VH of SEQ ID NO:11 and a variable light chain polypeptide VL of SEQ ID NO:14;
  (e) a variable heavy chain polypeptide comprising VH of SEQ ID NO:11 and a variable light chain polypeptide VL of SEQ ID NO:15;
  (f) a variable heavy chain polypeptide comprising VH of SEQ ID NO:12 and a variable light chain polypeptide VL of SEQ ID NO:13;
  (g) a variable heavy chain polypeptide comprising VH of SEQ ID NO:12 and a variable light chain polypeptide VL of SEQ ID NO:14;
  (h) a variable heavy chain polypeptide comprising VH of SEQ ID NO:12 and a variable light chain polypeptide VL of SEQ ID NO:15;
  wherein said anti-TfR antibody specifically binds to the transferrin receptor of SEQ ID NO:16.

In a specific embodiment, said recombinant anti-TfR antibody as defined above have one or more of the following properties:
  (i) They bind to the transferrin receptor with a $K_D$ of 10 nM or less, preferably with a $K_D$ of 1 nM or less, as measured by SPR, for example as described in the Examples below;
  (ii) it binds to the transferrin receptor with an EC50 of 0.1 µg/ml or below, preferably of 0.05 µg/ml or below, as measured in an ELISA assay as described in the Examples below;
  (iii) it induces apoptosis of HL-60 cell line to a level equal or superior to the induction level measured with the corresponding reference chimeric antibody having the parental murine variable regions with VH of SEQ ID NO:9 and VL of SEQ ID NO:10, for example as measured using the HL-60 apoptosis induction assay. Typically, an amount of 10 lag/ml of a recombinant antibody of the present disclosure may be assayed for induction of apoptosis of HL-60 cell line as compared to the same amount of the reference chimeric antibody with the parental murine variable regions of A24 comprising VH of SEQ ID NO:9 and VL of SEQ ID NO:10. Induction of apoptosis in the HL-60 apoptosis induction assay of a tested antibody is equal to a reference antibody if the percentage of positive cells as measured with the tested antibody is not significantly lower that the percentage of positive cells as measured with the reference antibody.

As used herein, a "corresponding" reference chimeric antibody refers to the reference antibody with an isotype constant region 100% identical to the isotype constant region of the antibody to be tested for a particular property, for example induction of apoptosis.

In certain embodiments that may be combined with the previous embodiments, an antibody provided herein is an antibody fragment of the above-defined antibodies.

Antibody fragments include, but are not limited to, Fab, Fab', Fab'-SH, F(ab')$_2$, Fv, Unibody, and scFv fragments, diabodies, single domain or nanobodies and other fragments.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells as described herein.

In certain embodiments, the antibody of the present disclosure is a humanized antibody. Typically, a non-human antibody is humanized to reduce immunogenicity to humans, while having at least the same affinity (or superior affinity) of the parental non-human antibody. In preferred embodiments, the antibodies of the present disclosure are humanized antibodies of the parent antibody A24.

Generally, a humanized antibody comprises one or more variable domains in which, CDRs, (or portions thereof) are derived from a non-human antibody, e.g. the murine A24 antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the A24 antibody from which the CDR residues are derived), e.g., to restore or improve antibody specificity or affinity. In some specific embodiments, some CDR residues in a humanized antibody are also substituted, e.g., to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc.

Natl Acad. Sci. USA 86: 10029-10033 (1989); U.S. Pat. Nos. 5,821,337, 7,527,791, 6,982,321, and 7,087,409; Kashmiri et al, Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al, Methods 36:61-68 (2005) and Klimka et al, Br. J. Cancer, 83:252-260 (2000) (describing the "guided selection" approach to FR shuffling).

Preferably the recombinant antibody according to the disclosure is a humanized silent antibody, preferably a humanized silent IgG1 or IgG4 antibody.

As used herein, the term "silent" antibody refers to an antibody that exhibits no or low ADCC activity as measured in an ADCC activity assay.

In one embodiment, the term "no or low ADCC activity" means that the silent antibody exhibit an ADCC activity that is at least below 10%, for example below 50% of the ADCC activity that is observed with the corresponding antibody with wild type human IgG1 isotype.

Silenced effector functions can be obtained by mutation in the Fc constant part of the antibodies and have been described in the Art: Strohl 2009 (AA & N297A); Baudino 2008, D265A (Baudino et al., J. Immunol. 181 (2008): 6664-69, Stroh), CO Biotechnology 20 (2009): 685-91). Examples of silent IgG1 antibodies comprise the so-called AA mutant comprising L234A and L235A mutation in the IgG1 Fc amino acid sequence. Another silent IgG1 antibody comprises the N297A mutation, which results in aglycosylated or non-glycosylated antibodies.

Antibodies with mutant amino acid sequences can be obtained by mutagenesis (e.g., site-directed or PCR-mediated mutagenesis) of the coding nucleic acid molecules, followed by testing of the encoded altered antibody for retained function (i.e., the functions set forth above) using the functional assays described herein.

Antibodies with Conservative Modifications

In certain embodiments, an antibody (or a binding protein comprising antigen binding portion thereof) of the disclosure has a heavy chain variable region comprising HCDR1, HCDR2, and HCDR3 sequences and a light chain variable region comprising LCDR1, LCDR2, and LCDR3 sequences, wherein one or more of these CDR sequences have specified amino acid sequences based on the mAb1 to mAb16 antibodies described herein or conservative modifications thereof, and wherein the antibody or protein retains the desired functional properties of the anti-TfR antibodies of the disclosure.

Desired functional properties of the anti-TfR antibodies includes without limitation:
(i) binding to the transferrin receptor with a $K_D$ of 10 nM or less, preferably with a $K_D$ of 1 nM or less, for example as measured by SPR assay, for example using Biacore®.
(ii) it binds to the transferrin receptor with an EC50 of 0.1 μg/ml or below, preferably of 0.05 μg/ml or below, as measured in an ELISA assay as described in the Examples below;
(iii) it induces apoptosis of HL-60 cell line to a level equal or superior to the induction level measured with the corresponding reference chimeric antibody having the parental murine variable regions with VH of SEQ ID NO:9 and VL of SEQ ID NO:10, for example as measured using the HL-60 apoptosis induction assay. Typically, an amount of 10 μg/ml of a recombinant antibody of the present disclosure may be assayed for induction of apoptosis of HL-60 cell line as compared to the same amount of the reference chimeric antibody with the parental murine variable regions of A24 comprising VH of SEQ ID NO:9 and VL of SEQ ID NO:10. Induction of apoptosis in the HL-60 apoptosis induction assay of a tested antibody is equal to a reference antibody if the percentage of positive cells as measured with the tested antibody is not significantly lower that the percentage of positive cells as measured with the reference antibody.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family, and the altered antibody can be tested for retained function using the functional assays described herein.

Modifications can be introduced into an antibody of the disclosure by standard techniques known in the art, such as site-directed mutagenesis and PCR-mediated mutagenesis.

Framework or Fc Engineering

Engineered antibodies of the disclosure include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody.

In particular, the company Antitope (Cambridge UK) has developed a range of proprietary technologies for assessing and removing immunogenicity, which are based on identifying the location of T cell epitopes in therapeutic antibodies and proteins. These technologies are summarized below:
iTope™—an in silico technology for prediction of peptide binding to human MHC class II alleles (Perry et al 2008 *Drugs in R&D*, 9(6):385-396).
TCED™—a database of known T cell epitopes identified in studies using EpiScreen™ T cell epitope mapping assays especially of antibody V regions (Bryson et al 2010 *Biodrugs* 24(1):1-8). The database can be interrogated by BLAST searching to identify common motifs (Altschul et al 1997 *Nucleic Acids Res.* (1997) 25:3389-3402).

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity.

Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below.

As used herein, the term "isotype constant region" or "Fc region" is used interchangeably to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the disclosure may comprise antibody populations with all K447 residues removed, antibody populations with no K447 residues removed, and antibody populations having a mixture of antibodies with and without the K447 residue.

In one specific embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chem 276:6591-6604).

In other embodiments, the Fc region is modified to decrease the ability of the antibody to mediate antibody dependent cellular cytotoxicity (ADCC) and/or to decrease the affinity of the antibody for an Fcγ receptor by modifying one or more amino acids. Such antibodies with decreased effector functions, and in particular decreased ADCC include silent antibodies.

In certain embodiments, the Fc domain of the IgG1 isotype is used. In some specific embodiments, a mutant variant of the IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant is IgG1 wherein Leucine is replaced by Alanine at amino acid positions 234 and 235 as described in J. Virol 2001 December; 75(24):12161-8 by Hezareh et al.

In certain embodiments, the Fc domain is a silent Fc mutant preventing glycosylation at position 297 of the Fc domain. For example, the Fc domain contains an amino acid substitution of asparagine at position 297. An example of such amino acid substitution is the replacement of N297 by a glycine or an alanine.

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1 176 195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the disclosure are produced by recombinant expression in a cell line which exhibits a hypofucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Another modification of the antibodies herein that is contemplated by the present disclosure is pegylation or hesylation or related technologies. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Another modification of the antibodies that is contemplated by the present disclosure is a conjugate or a protein fusion of at least the antigen-binding region of the antibody of the disclosure to serum protein, such as human serum albumin or a fragment thereof to increase half-life of the resulting molecule. Such approach is for example described in Ballance et al. EP 0 322 094.

Another possibility is a fusion of at least the antigen-binding region of the antibody of the disclosure to proteins capable of binding to serum proteins, such human serum albumin to increase half life of the resulting molecule. Such approach is for example described in Nygren et al., EP 0 486 525.

In one specific embodiment, the effector function or complement activation function of an antibody according to the disclosure has been reduced or eliminated relative to a wild-type antibody of the same isotype. In one aspect, the effector function is reduced or eliminated by a method selected from reduction of glycosylation of the antibody, modification of the antibody isotype to an isotype that naturally has reduced or eliminated effector function, and modification of the Fc region. In specific related embodiment, said isotype with reduced or eliminated effector function is IgG4 isotype.

Nucleic Acid Molecules Encoding Antibodies of the Disclosure

Also disclosed herein are the nucleic acid molecules that encode the anti-TfR antibodies or related proteins of the present disclosure. Examples of variable light chain nucleotide sequences are those encoding the variable light chain amino acid sequences of any one of mAb1 to mAb16, the latter sequences being easily derived from the Table 1 and Table 2, and using the genetic code and, optionally taking into account the codon bias depending on the host cell species.

The present disclosure also pertains to nucleic acid molecules that derive from the latter sequences having been optimized for protein expression in mammalian cells, for example, CHO cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the disclosure can be, for example, DNA or RNA and may or may not contain intronic sequences. In an embodiment, the nucleic acid may be present in a vector such as a phage display vector, or in a recombinant plasmid vector.

Nucleic acids of the disclosure can be obtained using standard molecular biology techniques. Once DNA fragments encoding, for example, VH and VL segments are obtained, these DNA fragments can be further manipulated by standard recombinant DNA techniques, for example to convert the variable region genes to full-length antibody chain genes, to Fab fragment genes or to an scFv gene. In these manipulations, a VL- or VH-encoding DNA fragment (for example VL and VH as defined in Table 1) is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes, for example human IgG1 isotype. In other embodiments, the heavy chain constant region is selected among IgG4 isotypes, for example human IgG4 isotype. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as to a Fab light chain gene) by operatively linking the VL-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the VH- and VL-encoding DNA fragments are operatively linked to another fragment encoding a flexible linker, e.g., encoding the amino acid sequence (Gly4-Ser)$_3$, such that the VH and VL sequences can be expressed as a contiguous single-chain protein, with the VL and VH regions joined by the flexible linker (see e.g., Bird et al., 1988 *Science* 242:423-426; Huston et al., 1988 *Proc. Natl. Acad. Sci. USA* 85:5879-5883; McCafferty et al., 1990 *Nature* 348:552-554).

Generation of Transfectomas Producing Monoclonal Antibodies

Antibodies of the present disclosure can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors disclosed herein carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, CA 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 *Mol. Cell. Biol.* 8:466-472).

In addition to the antibody chain genes and regulatory sequences, the recombinant expression vectors of the present disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the present disclosure in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the disclosure comprises one of the coding sequences of the heavy and light chains of any one of mAb1 to mAb16 operatively linked to suitable promoter sequences.

Mammalian host cells for expressing the recombinant antibodies of the disclosure include Chinese Hamster Ovary (CHO cells) (including dhfr-CHO cells, described Urlaub and Chasin, 1980 Proc. Natl. Acad. Sci. USA 77:4216-4220 used with a DHFR selectable marker, e.g., as described in R. J. Kaufman and P. A. Sharp, 1982 Mol. Biol. 159:601-621), CHOK1 dhfr+ cell lines, NSO myeloma cells, COS cells and SP2 cells, for example GS CHO cell lines together with GS Xceed™ gene expression system (Lonza).

When recombinant expression vectors encoding antibody genes are introduced into mammalian host cells, the antibodies are produced by culturing the host cells for a period of time sufficient for expression of the antibody in the host cells and, optionally, secretion of the antibody into the culture medium in which the host cells are grown. Antibodies can be recovered and purified for example from the culture medium after their secretion using standard protein purification methods (See for example Abhinav et al. 2007, Journal of Chromatography 848: 28-37).

In one specific embodiment, the host cell of the disclosure is a host cell transfected with an expression vector having the coding sequences suitable for the expression of mAb1-mAb16 respectively, operatively linked to suitable promoter sequences.

The latter host cells may then be further cultured under suitable conditions for the expression and production of an antibody of the disclosure selected from the group consisting of mAb1-mAb16 respectively.

Immunoconjugates

In another aspect, the present disclosure features an anti-TfR antibody as disclosed herein, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Cytotoxins can be conjugated to antibodies of the present disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Panowksi S et al. 2014 Jan. 1; 6(1): 34-45 for a review on antibody drug conjugates.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art.

Bispecific or Multispecific Molecules

In another aspect, it is further disclosed herein bispecific or multispecific molecules comprising an anti-TfR antibody of the present disclosure. An antibody can be derivatized or linked to another functional molecule, e.g., another peptide or protein (e.g., another antibody or ligand for a receptor) to generate a bispecific molecule that binds to at least two different binding sites or target molecules. The antibody may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for TfR, for example, one antigen-binding portion of any one of mAb1-mAb16 and a second binding specificity for a second target epitope. For example, the second target epitope is another epitope of TfR different from the first target epitope.

Additionally, for the embodiment in which the bispecific molecule is multi-specific, the molecule can further include a third binding specificity, in addition to the first and second target epitope.

In one embodiment, the bispecific molecules as disclosed herein comprise as a binding specificity at least one antibody, or an antibody fragment thereof, including, e.g., an Fab, Fab', F(ab')$_2$, Fv, Unibody or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules disclosed herein are murine, chimeric and humanized monoclonal antibodies.

The bispecific molecules of the present disclosure can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375).

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand ×Fab fusion protein. A bispecific molecule of the disclosure can be a single chain molecule comprising one single chain antibody and a binding determinant, or a single chain bispecific molecule comprising two binding determinants.

Binding of the bispecific molecules to their specific targets can be confirmed by, for example, enzyme-linked immunosorbent assay (ELISA), radioimmunoassay (REA), FACS analysis, bioassay (e.g., growth inhibition and apoptosis), or Western Blot assay. Each of these assays generally detects the presence of protein-antibody complexes of particular interest by employing a labeled reagent (e.g., an antibody) specific for the complex of interest.

The antibodies of the present disclosure may also be used to prepare artificial T cell receptor (also known as chimeric T cell receptors, or chimeric antigen receptors (CARs)). For example, the variable regions of antibodies may be used to form a scFv which is linked via a spacer to a transmembrane domain and a signaling endodomain of a TCR (for example CD3 zeta) and may be produced at the surface of T cells. Such CARs may be used in adoptive transfer therapy, for example for treating proliferative disorders.

Pharmaceutical Compositions

In another aspect, the present disclosure provides a composition, e.g., a pharmaceutical composition, containing one or a combination of antibodies disclosed herein, for example, one antibody selected from the group consisting of mAb1-mAb16, formulated together with a pharmaceutically acceptable carrier. Such compositions may include one or a combination of (e.g., two or more different) antibodies, or immunoconjugates or bispecific molecules as described above.

Pharmaceutical compositions disclosed herein also can be administered in combination therapy, i.e., combined with other agents. For example, the combination therapy can include an anti-TfR antibody of the present disclosure, for example one antibody selected from the group consisting of mAb1-mAb16, combined with at least one anti-viral, anti-inflammatory or another anti-proliferative agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., antibody, immunoconjugate, or bispecific molecule, may be coated in a material to protect the compound from the action of acids and other natural conditions that may inactivate the compound.

Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, parenteral, intranasal, intravenous, intramuscular, subcutaneous or intraocular administration and the like.

Preferably, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders or lyophilisates for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the disclosure can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the disclosure may be formulated within a therapeutic mixture to comprise about 0.0001 to 1.0 milligrams, or about 0.001 to 0.1 milligrams, or about 0.1 to 1.0 or even 1.0 to about 10 milligrams per dose. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present disclosure, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Uses and Methods of the Antibodies or Proteins of the Disclosure

The antibodies or proteins of the present disclosure have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

The antibodies of the disclosure can not only inhibit cell proliferation, but also induce apoptosis of highly proliferating cells, such as T cells.

It is the contemplated herein to use the anti-TfR antibody or protein of the present disclosure as a drug, in particular for use in treating, preventing or diagnosing cell proliferative disorders, such as tumors expressing a high level of TfR, more specifically, hematologic tumors, such as lymphoma, and in particular, ATL, MCL, Hodgkin Disease, Large B cell lymphoma, Peripheral T cell lymphoma, Acute leukaemia (Myeloid and Lymphoid) as well as solid tumors, such as Renal Carcinoma, Lung cancer (small cells), etc.

It is further disclosed antibodies of the present disclosure for use in treating, preventing or diagnosing HTLV-1 related disorders, in particular to reduce the viral load in inflammatory disorders associated with HTLV-1 infection, including HAM/TSP, polymyositis, and arthritis.

The disclosure also relates to methods for decreasing or suppressing transferrin uptake in human blood cells by administering a composition comprising a therapeutically efficient dose of the antibodies of the invention.

The antibodies or proteins for use as disclosed above may be administered as the sole active ingredient or in conjunction with, e.g. as an adjuvant to or in combination to, other drugs e.g. anti-viral, anti-inflammatory agents or cytotoxic, anti-proliferative, chemotherapy or anti-tumor agents, e.g. for the treatment or prevention of diseases mentioned above.

For example, the antibodies for use as disclosed above may be used in combination with AZT, IFN-alpha, anti-CD20 mAb, anti-CD25 mAb, chemotherapy agents.

Suitable antineoplastic agents may include without limitation, alkylating agents (such as cyclophosphamide, mechloretamine, chlorambucil, melphalan, nitrosureas, temozolomide), anthracyclines (such as daunorubicin, doxorubicin, epirubicin, idarubicin, mitoxantrone, valrubicin), taxanes (such as Paclitaxel, Docetaxel), epothilones, inhibitors of Topoisomerase I (such as Irinotecan or Topotecan), inhibitors of Topoisomerase II (such as Etoposide, teniposide, or Tafluposide), nucleotide analogs and precursor analogs (such as azacitidine, azathioprine, capecitabine, cytarabine, flurouracil, gemcitabine, hydroxyurea, mercaptopurine, methotrexate, or Tioguanine), peptide antibiotics (such as carboplatin, cisplatin and oxaliplatin), retinoids (such as tretinoin, alitretinoin, bexarotene), vinca alkaloids and derivatives (such as vinblastine, vincristine, vindesine, vinorelbine), targeted therapies such as kinase inhibitors (such as Ibrutinib, Idelalisib, Erlotinib, Gefitinib, Imatinib, Vemurafenib, Vismodegib), proteasome inhibitors (such as bortezomib, carfilzomib), histone deacetylase inhibitors (such as Vorinostat or Romidepsin).

In accordance with the foregoing the present disclosure provides in a yet further aspect:

A method as defined above comprising co-administration, e.g. concomitantly or in sequence, of a therapeutically effective amount of an anti-TfR antibody or protein of the disclosure, and at least one second drug substance, said second drug substance being a anti-viral or anti-proliferative agent, e.g. as indicated above.

In one embodiment, the antibodies or proteins of the disclosure can be used to detect levels of TfR, or levels of cells that contain TfR. This can be achieved, for example, by contacting a sample (such as an in vitro sample) and a control sample with the anti-TfR antibody under conditions that allow for the formation of a complex between the antibody and TfR. Any complexes formed between the antibody and TfR are detected and compared in the sample and the control. For example, standard detection methods, well known in the art, such as ELISA and flow cytometric assays, can be performed using the compositions of the disclosure.

Accordingly, in one aspect, the disclosure further provides methods for detecting the presence of TfR (e.g., human TfR antigen) in a sample, or measuring the amount of TfR, comprising contacting the sample, and a control sample, with an antibody or protein of the disclosure, or an antigen binding region thereof, which specifically binds to TfR, under conditions that allow for formation of a complex between the antibody or portion thereof and TfR. The formation of a complex is then detected, wherein a difference in complex formation between the sample compared to the control sample is indicative of the presence of TfR in the sample.

Also within the scope of the present disclosure are kits consisting of the compositions (e.g., antibodies, proteins, humanized antibodies, conjugated antibodies and multispecific molecules) disclosed herein and instructions for use. The kit can further contain a least one additional reagent, or one or more additional antibodies or proteins (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an anti-TfR antibody treatment, as defined above.

The invention having been fully described is now further illustrated by the following examples, which are illustrative only and are not meant to be further limiting.

EXAMPLES

Methods

1. Affinity Testing by ELISA

For the determination of the specificity of the antibody an ELISA test may be applied using the following protocol.

Recombinant human TfR (as obtained from R&D Systems, Catalog number 2474-TR) are directly coated on a 96 well plate overnight and washed twice before incubation with several dilutions (10) of the antibody (murine and humanized mAb) (dilution may start at the concentration of 50 µg/ml through 0,001 ug/ml) and incubate 1 hour at room temperature. After two washes a secondary antibody Goat-anti Human IgG is incubated Incubate 1 hour at room temperature in the dark, washed twice and incubated with the TMB solution for 10 minutes before reading the absorbance at 450 nm.

2. Affinity Determination Using Surface Plasmon Resonance (Biacore System)

For determination of $K_D$ values, surface plasmon resonance technology may be applied using the Biacore™ technology as described below:

Histidin-tagged human TfR (as obtained from R&D Systems, Catalog number 2474-TR) was bound after passage on covalently immobilized Penta-His mAb CM5 sensor chip. Ten different concentrations of antibody (1 to 500 nM) were injected across the anti-His/TfR-His surface for 4 minutes and the dissociation complexes was followed for 5 minutes. Both association and dissociation profiles are analyzed with a nonlinear square algorithm implemented in the BIAevaluation software using single-exponential functions of time.

3. ADCC Assay

Antibody-dependent cell-mediated cytotoxicity is a desirable mechanism for killing target cancer cells using antibody-based drugs. The antibody binds to target antigens on the cell surface. When the Fc effector portion of target-bound antibodies also binds to FcγRIIIa receptors on the cell surface of effector cells (natural killer cells predominantly), multiple cross-linking of the two cell types occurs, leading to pathway activation of ADCC. Killing of target cells is an endpoint of this pathway activation and is used in classic ADCC bioassays, which use donor peripheral blood mononuclear cells (PBMCs) or the natural killer (NK) cell subpopulation as effector cells. The ADCC Reporter Bioassay Complete Kit (Promega, G7015) contains all of the components and reagents necessary to perform an anti-CD20-based ADCC Reporter Bioassay. The ADCC Reporter Bioassay uses an alternative readout at an earner point in ADCC pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor and an NFAT response element driving expression of firefly luciferase as effector cells. Antibody biological activity in ADCC is quantified through the luciferase produced as a result of NFAT pathway activation; luciferase activity in the effector cell is quantified with luminescence readout. As a positive control to compare with humanized mAb, the kit provides an anti-CD20 antibody.

4. HL-60 and PHA Activated T Cell Apoptosis Induction Assay

For the apoptosis assay, cells were incubated in the 24 wells plate at the concentration of $100.10^3$ cells per well in 400 µl. Subsequently, cells are incubated 3 and 4 days in presence of several dilutions on the murine or the humanized antibody (from 200 µg/ml till 3 µg/ml). After the incubation time, cells are centrifuged and labelled in presence of Annexin V and Tropo 3 for 15 minutes before Flow cytometry analysis.

5. Productivity Assay (400 ml)

For the test of productivity, VH genes were synthesized and cloned into expression vector pXCIgG (ΔK) for heavy chain. Light chains were previously sub-cloned into pXCKappa vector. The 16 antibodies were transiently expressed in CHOK1SV GS-KO cells in a volume of 400 ml (shake flask). The produced antibodies were purified using Protein A affinity chromatography. Antibody concentrations were determined using a predicted extinction coefficient (1.49) for all antibody variants. The integrity of the variants was determined by SDS-PAGE in both reducing and non-reducing conditions.

Examples mAb1 to mAb16

The Examples mAb1 to mAb16 as described in Table 1 can be produced using conventional antibody recombinant production and purification processes.

For example, the coding sequences have been cloned into a production vector for recombinant expression in mammalian production cell line.

The following Tables 4 and 5 provides detailed amino acid and nucleotide sequences useful for practicing the invention, and in particular for producing the nucleic acids, expression vectors and antibodies of the present disclosure.

TABLE 4

Brief description of useful amino acid and nucleotide sequences for practicing the invention

| SEQ ID NO: | Description of the sequence |
|---|---|
| 1 | HCDR1 amino acid sequence of A24, VH4 and VH5 |
| 2 | HCDR2 amino acid sequence of A24, VH4 and VH5 |
| 3 | HCDR3 amino acid sequence of A24, VH4 and VH5 |
| 4 | LCDR1 amino acid sequence of A24, VL4, VL5 and VL6 |
| 5 | LCDR2 amino acid sequence of VL4 |
| 6 | LCDR3 amino acid sequence of A24, VL4, VL5 and VL6 |
| 7 | LCDR2 amino acid sequence of A24 |
| 8 | LCDR2 amino acid sequence of VL5 |
| 9 | VH0 amino acid sequence of A24 |
| 10 | VL0 amino acid sequence of A24 |
| 11 | VH4 amino acid sequence |
| 12 | VH5 amino acid sequence |
| 13 | VL4 amino acid sequence |
| 14 | VL5 amino acid sequence |
| 15 | VL6 amino acid sequence |
| 16 | Human transferrin receptor amino acid sequence |
| 17 | Full length light chain of mAb1, mAb3, mAb5, mAb7, mAb9, mAb11, mAb13, mAb15 (with VL4) |
| 18 | Full length heavy chain of mAb1, mAb2 (with VH4-IgG4 isotype) |
| 19 | Nucleotide sequence encoding Full length light chain of mAb1, mAb3, mAb5, mAb7, mAb9, mAb11, mAb13, mAb15 (with VL4) of SEQ ID NO: 19 |
| 20 | Nucleotide sequence encoding Full length heavy chain of mAb1, mAb2 (with VH4-IgG4 isotype) of SEQ ID NO: 22 |

TABLE 5

Brief description of useful amino acid and nucleotide sequences for practicing the invention

| SEQ ID NO: | Describes the amino acid or nucleotide sequence below: |
|---|---|
| 1 | GYTFTNQ |
| 2 | NTYTGE |
| 3 | EGWDSMDY |
| 4 | SASSSVNYMH |
| 5 | STSNRAT |
| 6 | QQRSSYPLT |
| 7 | STSNLAS |
| 8 | STSNRAS |
| 9 | QIQLVQSGPELKKPGETVKISCKASGYTFTNQGMNWVKQAPGKGLKWMGWINTYTGEPINADDFKGRFAISLETSASTAYLQINNLKNEDMATYFCVREGWDSMDYWGQGTSVTVSS |
| 10 | QIVLTQSPAIMSASPGEKVTITCSASSSVNYMHWFQQKPGTSPKLWIYSTSNLASGVPARFSGSGSGTSYSLTISRMEAEDAATYYCQQRSSYPLTFGAGTKLELKR |
| 11 | QVQLVQSGPELKKPGASVKVSCKASGYTFTNQGMNWVKQAPGKGLKWMGWINTYTGEPINADDFKGRFVISLDTSASTAYLQISSLKAEDTAVYFCVREGWDSMDYWGQGTSVTVSS |
| 12 | MEWSWVFLFFLSVTTGVHSQVQLVQSGPELKKPGASVKVSCKASGYTFTNQGMNWVKQAPGKGLKWMGWINTYTGEPINADDFKGRFVISLETSASTAYLQISNLKNEDTAVYFCVREGWDSMDYWGQGTSVTVSS |

TABLE 5-continued

Brief description of useful amino acid and nucleotide sequences for practicing the invention

| SEQ ID NO: | Describes the amino acid or nucleotide sequence below: |
|---|---|
| 13 | QIVLTQSPATLSVSPGERATLSCSASSSVNYMHWFQQKPGQSPRLLIYSTS NRATGIPARFSGSGSGTSYTLTISSLEPEDFAVYYCQQRSSYPLTFGQGTKL EIKR |
| 14 | QIVLTQSPATLSLSPGERATLSCSASSSVNYMHWFQQKPGQSPRLLIYSTSN RASGVPARFSGSGSGTSYTLTISRLEPEDFAVYYCQQRSSYPLTFGQGTKL EIKR |
| 15 | QIVLTQSPATLSLSPGERATLSCSASSSVNYMHWFQQKPGQSPRLLIYSTSN LASGVPARFSGSGSGTSYTLTISRLEPEDAAVYYCQQRSSYPLTFGAGTKL ELKR |
| 16 | MMDQARSAFSNLFGGEPLSYTRFSLARQVDGDNSHVEMKLAVDEEENADN NTKANVTKPKRCSGSICYGTIAVIVFFLIGFMIGYLGYCKGVEPKTECERLAG TESPVREEPGEDFPAARRLYWDDLKRKLSEKLDSTDFTGTIKLLNENSYVPR EAGSQKDENLALYVENQFREFKLSKVWRDQHFVKIQVKDSAQNSVIIVDKN GRLVYLVENPGGYVAYSKAATVTGKLVHANFGTKKDFEDLYTPVNGSIVIVR AGKITFAEKVANAESLNAIGVLIYMDQTKFPIVNAELSFFGHAHLGTGDPYTP GFPSFNHTQFPPSRSSGLPNIPVQTISRAAAEKLFGNMEGDCPSDWKTDST CRMVTSESKNVKLTVSNVLKEIKILNIFGVIKGFVEPDHYVVVGAQRDAWGP GAAKSGVGTALLLKLAQMFSDMVLKDGFQPSRSIIFASWSAGDFGSVGATE WLEGYLSSLHLKAFTYINLDKAVLGTSNFKVSASPLLYTLIEKTMQNVKHPVT GQFLYQDSNWASKVEKLTLDNAAFPFLAYSGIPAVSFCFCEDTDYPYLGTT MDTYKELIERIPELNKVARAAAEVAGQFVIKLTHDVELNLDYERYNSQLLSFV RDLNQYRADIKEMGLSLQWLYSARGDFFRATSRLTTDFGNAEKTDRFVMKK LNDRVMRVEYHFLSPYVSPKESPFRHVFWGSGSHTLPALLENLKLRKQNNG AFNETLFRNQLALATWTIQGAANALSGDVWDIDNEF |
| 17 | MSVPTQVLGLLLLWLTDARCQIVLTQSPATLSVSPGERATLSCSASSSVNYM HWFQQKPGQSPRLLIYSTSNRATGIPARFSGSGSGTSYTLTISSLEPEDFAV YYCQQRSSYPLTFGQGTKLEIKRTVAAPSVFIFPPSDEQLKSGTASVVCLLN NFYPREAKVQWKVDNALQSGNSQESVTEQDSKDSTYSLSSTLTLSKADYEK HKVYACEVTHQGLSSPVTKSFNRGEC |
| 18 | MEWSWVFLFFLSVTTGVHSQVQLVQSGPELKKPGASVKVSCKASGYTFTN QGMNWVKQAPGKGLKWMGWINTYTGEPINADDFKGRFVISLDTSASTAYL QISSLKAEDTAVYFCVREGWDSMDYWGQGTSVTVSSASTKGPSVFPPLAPC SRSTSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPEFLG GPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKA KGQPREPQVYTLPPSQEEMTKNQVSLTCLVKGFYPSDIAVEWESNGQPEN NYKTTPPVLDSDGSFFLYSRLTVDKSRWQEGNVFSCSVMHEALHNHYTQK SLSLSLG |
| 19 | AAGCTTGCCGCCACCATGTCCGTGCCTACCCAGGTGCTGGGACTGCTG CTGCTGTGGCTGACCGATGCCAGGTGCCAGATCGTGCTGACCCAGTCT CCTGCCACCCTGTCTGTGTCTCCCGGCGAGAGAGCTACCCTGTCCTGCT CCGCCTCCTCCTCCGTGAACTACATGCACTGGTTCCAGCAGAAGCCCGG CCAGTCCCCCAGACTGCTGATCTACTCCACCTCCAACCGGGCCACCGG CATCCCTGCCAGATTTTCCGGCTCTGGCTCCGGCACCTCCTATACCCTG ACCATCTCCAGCCTGGAACCCGAGGACTTCGCCGTGTACTACTGCCAGC AGCGGTCCTCCTACCCCCTGACCTTTGGCCAGGGCACCAAGCTGGAAAT CAAGCGTACGGTGGCCGCTCCCAGCGTGTTCATCTTCCCCCCAAGCGA CGAGCAGCTGAAGAGCGGCACCGCCAGCGTGGTGTGTCTGCTGAACAA CTTCTACCCCAGGGAGGCCAAGGTGCAGTGGAAGGTGGACAACGCCCT GCAGAGCGGCAACAGCCAGGAGAGCGTCACCGAGCAGGACAGCAAGG ACTCCACCTACAGCCTGAGCAGCACCCTGACCCTGAGCAAGGCCGACTA CGAGAAGCACAAGGTGTACGCCTGTGAGGTGACCCACCAGGGCCTGTC CAGCCCCGTGACCAAGAGCTTCAACAGGGGCGAGTGCTGATGAATTC |
| 20 | AAGCTTGCCGCCACCATGGAATGGTCCTGGGTGTTCCTGTTCTTCCTGT CCGTGACCACCGGCGTGCACTCCCAGGTGCAGCTGGTGCAGTCTGGCC CCGAGCTGAAGAAACCTGGCGCCTCCGTGAAGGTGTCCTGCAAGGCTT CCGGCTACACCTTTACAAACCAGGGCATGAACTGGGTCAAGCAGGCCCC TGGCAAGGGCCTGAAGTGGATGGGCTGGATCAACACCTACACCGGCGA GCCCATCAACGCCGACGACTTCAAGGGCAGATTCGTGATCTCCCTGGAC ACCTCCGCCTCCACCGCCTACCTGCAGATCAGCTCTCTGAAGGCCGAG GATACCGCCGTGTACTTCTGCGTGCGGGAAGGCTGGGACTCCATGGAC TATTGGGGCCAGGGCACCTCCGTGACCGTGTCTAGCGCTTCTACAAAGG GCCCAAGCGTGTTCCCCCCTGGCCCCCTGCTCCAGAAGCACCAGCGAGA GCACAGCCGCCCTGGGCTGCCTGGTGAAGGACTACTTCCCCGAGCCCG |

TABLE 5-continued

Brief description of useful amino acid and nucleotide sequences
for practicing the invention SEQ ID
NO: Describes the amino acid or nucleotide sequence below:

```
TGACCGTGTCCTGGAACAGCGGAGCCCTGACCAGCGGCGTGCACACCT
TCCCCGCCGTGCTGCAGAGCAGCGGCCTGTACAGCCTGAGCAGCGTGG
TGACCGTGCCCAGCAGCAGCCTGGGCACCAAGACCTACACCTGTAACG
TGGACCACAAGCCCAGCAACACCAAGGTGGACAAGAGGGTGGAGAGCA
AGTACGGCCCACCCTGCCCCCCCTGCCCAGCCCCCGAGTTCCTGGGCG
GACCCAGCGTGTTCCTGTTCCCCCCCAAGCCCAAGGACACCCTGATGAT
CAGCAGAACCCCCGAGGTGACCTGTGTGGTGGTGGACGTGTCCCAGGA
GGACCCCGAGGTCCAGTTCAACTGGTACGTGGACGGCGTGGAGGTGCA
CAACGCCAAGACCAAGCCCAGAGAGGAGCAGTTTAACAGCACCTACCG
GGTGGTGTCCGTGCTGACCGTGCTGCACCAGGACTGGCTGAACGGCAA
AGAGTACAAGTGTAAGGTCTCCAACAAGGGCCTGCCAAGCAGCATCGAA
AAGACCATCAGCAAGGCCAAGGGCCAGCCTAGAGAGCCCCAGGTCTAC
ACCCTGCCACCCAGCCAAGAGGAGATGACCAAGAACCAGGTGTCCCTG
ACCTGTCTGGTGAAGGGCTTCTACCCAAGCGACATCGCCGTGGAGTGG
GAGAGCAACGGCCAGCCCGAGAACAACTACAAGACCACCCCCCCAGTG
CTGGACAGCGACGGCAGCTTCTTCCTGTACAGCAGGCTGACCGTGGAC
AAGTCCAGATGGCAGGAGGGCAACGTCTTTAGCTGCTCCGTGATGCACG
AGGCCCTGCACAACCACTACACCCAGAAGAGCCTGAGCCTGTCCCTGG
GCTGATGAATTC
```

Results

Designing Functional Humanized Antibodies of A24

Humanization

The humanization procedure was performed as outlined below:
1. Parental antibody domains and regions were identified.
2. Parental antibody sequences were aligned to a set of reference sequences.
3. A 3D structural model of the Parental protein was constructed.
4. Based on the collected data an initial assessment of the possibility to substitute each position was made and positions were categorized.
5. Structural models of humanized variants were constructed when required and compared to the Parental model for structural analysis of potential substitutions.
6. The CDR-grafting was done by analyzing positions differing between the Parental and Acceptor sequences. Contributing positions were generally retained and only substituted if such substitutions are relatively favorable based on their potential influence on affinity and compatibility with the Acceptor framework.
7. A final set of variant combinations of humanized light and heavy chains was designed.

Sequence Annotation

The Conserved Domain Database (CDD) (Marchler-Bauer et al. 2011) was used to determine the domain content of each amino-acid chain and the approximate boundaries of each domain. Variable domain boundaries were exactly determined along with the boundaries of the complementarity-determining regions (CDRs) according to several commonly used definitions (Kabat and Wu 1991, Chothia and Lesk 1987 updated in Al-Lazikani et al. 1997, Honegger and Plücktuhn 2001). The updated Chothia CDR definition (Al-Lazikani et al. 1997) has been used and positional numbering in which case Chothia 1987 numbering has been used.

Sequence Alignments

Multiple alignments of the Parental sequence to the mouse and human germline sequences were generated using MAFFT (Katoh et al. 2002) and entries in each alignment were ordered according to the sequence identity (SeqID) to the Parental sequence. Reference sets were reduced to a unique set of sequences by clustering at 100% SeqID and excluding redundant entries.

Identification of Residues at Critical Positions

Antibody Fv's have a number of critical positions that make up the VH/VL inter chain interface or are responsible for the discrete set of canonical structures that has been defined for five of the CDRs (Chothia and Lesk 1987, Martin and Thornton 1996, Al Laziniki et al. 1997); these positions should be considered in detail before substitutions are proposed for them. Based on the Parental antibody sequence alignment to the human germlines, the closest matching entries were identified. The identification of the optimal human germline as Acceptor was based on the ordered criteria listed below:
1. Sequence identity across the framework
2. Identical or compatible inter-chain interface residues
3. Support loops with the Parental CDRs canonical conformations
4. The combination of heavy and light germlines are found in expressed antibodies Construction of 3D Models Structural models of the Fv-region for the parental murine antibody and variants thereof, were generated using Lonza's modelling platform. Candidate structural template fragments for the framework (FR) and complementarity-determining regions (CDRs) as well as the full Fv were scored, ranked and selected from an in-house antibody database based on their sequence identity to the target, as well as qualitative crystallographic measures of the template structure, such as the resolution (in Angstrom (A)).

In order to structurally align the CDRs to the FR templates, five residues on either side of the CDR were included in the CDR template. An alignment of the fragments was generated based on overlapping segments and a structural sequence alignment generated. The template fragments along with the alignment were processed by MODELLER (Sali et al. 1993).

This protocol creates conformational restraints derived from the set of aligned structural templates. An ensemble of structures that satisfy the restraints is created by conjugate gradient and simulated annealing optimization procedures.

One or more model structures are selected from this ensemble on the basis of an energy score, derived from the score of the protein structure and satisfaction of the conformational restraints. The models were inspected and the side chains of the positions, which differ between the target and template, were optimized using a side chain optimization algorithm and energy minimized.

A suite of visualization and computational tools were used to assess the conformational variability of the CDRs, as well as the core and local packing of the domains and regions and a surface analysis to select one or more preferred models.

Comparison of Modelled Structures

Structural models for the Parental and humanised Fv-regions are modelled individually, as described previously, to ensure the variant models are not constructed with any inherent bias towards the Parental model structure. However, the high sequence identity of the humanised variants to the Parental sequence often results in identical structural templates being selected for many models.

To assess the impact of different substitutions on affinity and stability, a number of structural criteria are used. The solvent accessibility, local atomic packing and location of the substitution relative to the predicted antigen binding interface or the Fv dimer interface are key criteria. The observation of an unfavourable solvation state, bad interatomic contacts or the poor placement of an inappropriate residue at a key position leads to the rejection of a potential substitution. Other criteria, such as electrostatic effects, hydrogen bonding patterns or potential hydrogen bonding patterns are also used to assess the suitability of a substitution. Some positions are more suitable than others for the acceptance of substitutions as a set of critical positions play a role in supporting the canonical class of CDRs, the packing of the individual domain cores or the inter-domain interfaces.

Assessment of Potential Substitutions

All positions differing between the Parental and Acceptor frameworks or near predicted epitopes were assessed based on their potential impact on binding affinity and stability.

There are many factors that contribute to this categorization, originating from concerns over both affinity and stability. The factors contributing to the classification are:

Positions responsible for antigen binding
Critical positions
Conserved residues within the VH/VL interface
Positions determining CDR canonical class
Distance from the CDRs
Conservation or variation at the position in the reference alignment
Solvent accessibility
Local atomic packing
Local secondary structure
Electrostatic effects
Hydrogen bonding patterns
Hydrogen bonding potential
Post-translational modifications
N-glycosylation
Deamidation Critical positions are initially defined as those in the Chothia CDRs, determined to be at critical positions in the VH/VL interface; at positions that help determine the CDR conformation or that are highly conserved in the reference alignment. Many positions are conserved and will only accept a small set, or only one, type of amino acid.

Optimal Acceptor Framework Selection

Sequence alignments comparing parental variable domains to the human germline were generated. Given overall sequence identity, matching interface positions and similarly classed CDR canonical positions the light chain still had several equally suitable Acceptor frameworks; often one was slightly more suitable for one region but less for another. Consequently two light chain Acceptor frameworks were selected VK6-A26 and VK3-L6.

The heavy chain best matched the human germline VH7-7-4.1. The VH7 germline family contains only one member, which can be incorporated into the VH1 family (Knappik et al. 2000). As it is likely that the VH7 germline is found less frequently than the VH1 germline it was deemed preferable to use the latter as an Acceptor framework. However, when the positions with potential back-mutations were analyzed it became clear that the VH7 germline already contained the appropriate residues. Hence two IGHV germlines were used as Acceptor frameworks; VH7-7-4.1 and VH1-1-03.

The J-segment genes were compared to the A24 Parental sequences over FR4 and J-segments. JK4 and JH4 were identified as the best match for the light and heavy chain respectively, and were therefore selected as the J-segment Acceptor frameworks.

Humanization

A list of all the positions with differing residues between the Parental and Acceptor framework was generated. All positions were analyzed and considered both in isolation and in the context of other potential substitutions. Each position was ranked and a suggestion about which residues to substitute and evaluate in humanized variants was made. Three humanized chains were proposed for the light chain; one using Acceptor VK3-L6 and two with Acceptor VK6-A26 where one had additional Contributing positions retained from the Parental sequence (back-mutations). Two humanized chains were proposed for the heavy chain; one using each selected Acceptor. The VH7-7-4.1 graft is the more conservative; see Table 6.

TABLE 6

Humanised chains

| Chain | Name | Description |
|---|---|---|
| L | VL1 | A24 humanized light chain with Acceptor VK6-A26 |
| L | VL2 | A24 humanized light chain Acceptor VK6-A26 with further back mutations |
| L | VL3 | A24 humanized light chain with Acceptor VK3-L6 |
| H | VH1 | A24 humanized heavy chain with Acceptor VH7-7-4.1 |
| H | VH2 | A24 humanized heavy chain with Acceptor VH1-1-03 |

First Generation of 6 Humanized Antibodies Failed to Maintain A24 Functional Properties Based on the methods described in the previous section, we first designed 3 humanized light chain variants of A24, (hereafter called VL1, VL2 and VL3) and 2 humanized heavy chain variants of A24 (hereafter called VH1 and VH2). We called VH0 and VL0 the corresponding VH and VL of A24.

We generated the following 6 humanized antibodies with the following combination of humanized VH and VL and human IgG1 isotype:

INA01 Variant 1 humanized antibody: VH1/VL1

INA01 Variant 2 humanized antibody: VH2/VL1

INA01 Variant 3 humanized antibody: VH1/VL2

INA01 Variant 4 humanized antibody: VH2/VL2
INA01 Variant 5 humanized antibody: VH1/VL3
INA01 Variant 6 humanized antibody: VH2/VL3

We assayed these 6 humanized antibodies for induction of apoptosis of HL-60 cells according to the assay as described above and compared such property of inducing apoptosis with the chimeric form of the reference murine antibody A24 (VH0/VL0) with the same human IgG1 isotype. The results are shown in FIG. 1.

Figure 1:
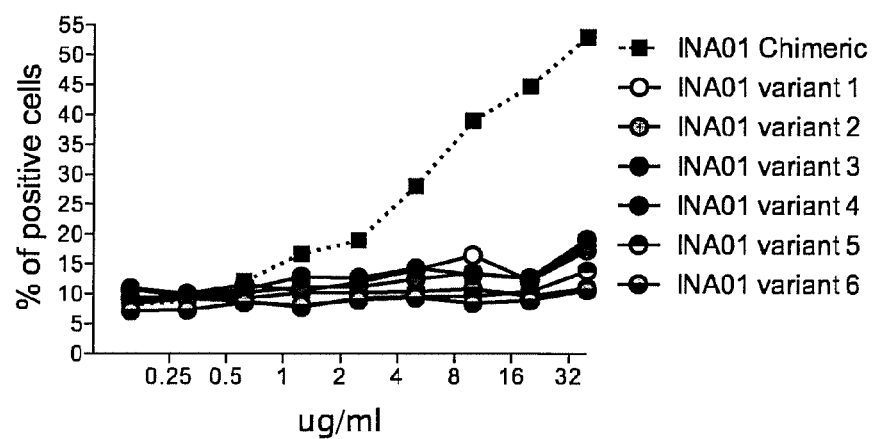
FIG. 1 is a graph showing the lack of induction of apoptosis of the first 6 humanized variants of INA01 (INA01 variants 1-6) as compared to the chimeric INA01 antibody with parental A24 variable regions as measured according to the HL-60 apoptosis induction assay.

As shown in FIG. 1, we surprisingly found that all test humanized antibodies had lost their binding properties. This is particularly surprising considering the fact that, some of the variants had all 6 CDRs in common with its parental murine A24 antibody.

Generation of 5 New Humanized Antibodies

We then designed a new heavy chain (VH3) and generated the following humanized antibody:

INA01 Variant 7 humanized antibody: VH0/VL1
INA01 Variant 8 humanized antibody: VH3/VL1
INA01 Variant 9 humanized antibody: VH3/VL2
INA01 Variant 10 humanized antibody: VH3/VL3
INA01 Variant 11 humanized antibody: VH3/VL0

Again, we tested these humanized antibodies for their capacity to induce apoptosis based on HL-60 apoptosis induction assay as described above as compared to the chimeric INA01 corresponding to an antibody with parental murine A24 variable regions and human IgG1 isotype. The results are shown in FIG. 2.

Figure 2:
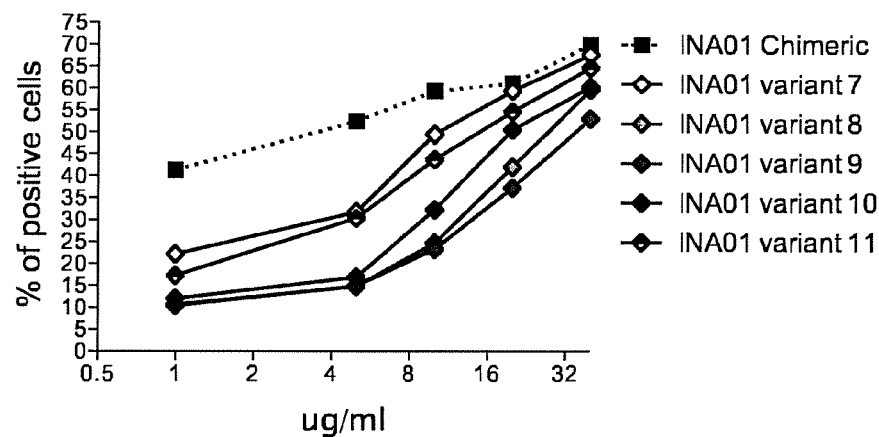
FIG. 2 is a graph showing improved apoptosis effect of the second round of humanized variants (INA01 variants 7-11), however still below the chimeric INA01 antibody with parental A24 variable regions, as measured according to the HL-60 apoptosis induction assay.

As shown in FIG. 2, the humanized antibodies have again lost at least partially their properties to induce apoptosis.

Generation of 6 New Humanized Antibodies

Based on the results obtained with the above 3 new antibodies, we designed again 3 new light chains and 2 new heavy chains.

In particular, we used in silico analysis to predict changes of amino acid (whether in the framework or CDR regions) that reduce immunogenicity while still maintaining the advantageous properties of the parent antibody A24.

In the current analysis, iTope™ was used to analyze the A24 derived sequences for promiscuous high affinity binders to human MHC class II. Promiscuous high affinity MHC class II binding peptides are thought to correlate with the presence of T cell epitopes (Hill et al 2003 Arthritis Res Ther. (2003) 1:R40-R48) although medium and low affinity binders can also trigger T cell responses. Thus iTope™ was used to provide a useful initial "low resolution" screen for the location of potential T cell epitopes. In addition, the sequences were analysed by TCED™ BLAST search to locate any T cell epitopes previously identified by EpiScreen™ analysis of other protein sequence.

As shown in Table 7; in silico analysis iTope™ revealed that amino acid substitutions L53R and/or S55T in LCDR2 may reduce immunogenicity.

We therefore decided to test 3 new light chains, one (VL4) including 2 amino acid substitutions in LCDR2 as compared to LCDR2 of A24, one (VL5) including only one amino acid substitution in LCDR2, and one (VL6) having identical LCDR2 as compared to A24.

The following 6 new humanized antibodies were generated with IgG1 isotype constant region.

INA01 variant 12 VH4/VL4
INA01 variant 13 VH5/VL4
INA01 variant 14 VH4/VL5
INA01 variant 15 VH5/VL5
INA01 variant 16 VH4/VL6
INA01 variant 17 VH5/VL6

FIG. 5a shows the alignment of VL4, VL5, VL6 with VL of A24 antibody.

FIG. 5b shows the alignment of VH4 and VH5 with VH of A24 antibody.

We tested these humanized antibodies for their capacity to induce apoptosis based on HL-60 72 h apoptosis assay as described above and as compared to the chimeric INA01 corresponding to an antibody with parental murine A24 variable regions and human IgG1 isotype. The results are shown in FIG. 3.

Figure 3:
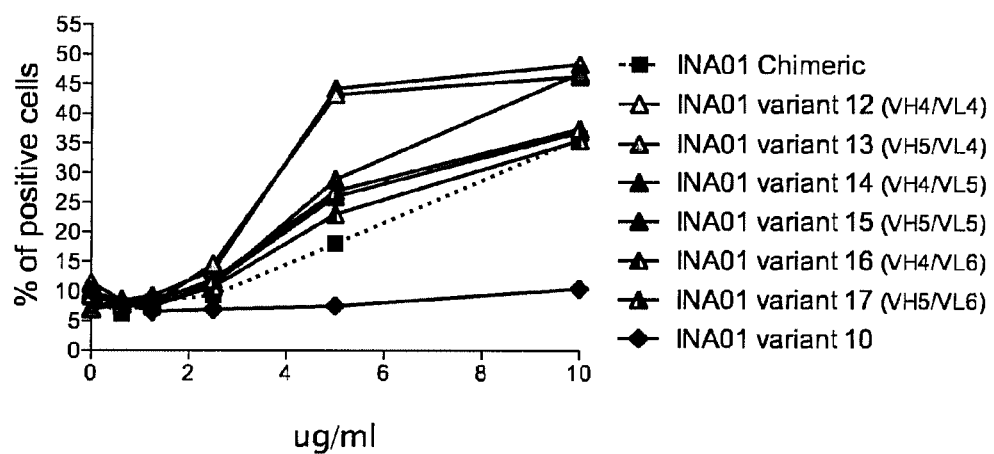
FIG. 3 is a graph showing effective induction of apoptosis of the third round of humanized variants (INA01 variants 12-17), superior to the chimeric INA01 antibody with parental A24 variable regions, as measured according to the HL-60 apoptosis induction assay.

As shown in FIG. 3, all 6 new tested humanized antibodies have now similar or even superior properties as compared to the chimeric INA01 corresponding to an antibody with parental murine A24 variable regions and human IgG1 isotype.

In particular antibodies variant 12 and variant 13 with 2 amino acid substitutions in LCDR2 now surprisingly showed superior induction properties as compared to the parent chimeric INA01 antibody.

Conversion to IgG

In order to express full length IgG, variable domain fragments of heavy ($V_H$) and light chains ($V_L$) of the four lead candidates variants 12, 14, 15 and 17 were subcloned from Fab expression vectors into appropriate expression vectors for human IgG4, human IgG1 wild type, human IgG1L234AL235A and human IgG1N297A, said human IgG1 L234AL235A being herein referred as "AA", resulting in expression vectors for the production of the 16 antibodies according to the invention, mAb1-mAb16 as described in Table 8 below:

TABLE 8

Description of the variable regions
and IgG Fc region of mAb1-mAb16

| Example | variable region and IgG Fc region |
|---|---|
| mAb1 | VH4/VL4 with IgG4 Fc region |
| mAb2 | VH4/VL5 with IgG4 Fc region |

TABLE 7

| Sequence | p1 Anchor | p1 Location | iTope ™ Residues | MHC II Ligands | High Affinity | TCED ™ Homology | |
|---|---|---|---|---|---|---|---|
| IYS01 VL4 | I48 | Fw2 | IYSTSNRAT | 7 | 2 | ..A...L.S | SEQ ID NO: 21 |
| IYS01 VL5 | I48 | Fw2 | IYSTSNRAS | 21 | 11 | ..A...L.. | SEQ ID NO: 22 |
| IYS01 VL6 | I48 | Fw2 | IYSTSNLAS | 26 | 15 | ..A..... | SEQ ID NO: 23 |
| MHC II pocket positions: | | | 1  4 67 9 | | | 1  4 67 9 | |

TABLE 8-continued

Description of the variable regions
and IgG Fc region of mAb1-mAb16

| Example | variable region and IgG Fc region |
|---|---|
| mAb3 | VH5/VL4 with IgG4 Fc region |
| mAb4 | VH5/VL6 with IgG4 Fc region |
| mAb5 | VH4/VL4 with IgG1 Fc region |
| mAb6 | VH4/VL5 with IgG1 Fc region |
| mAb7 | VH5/VL4 with IgG1 Fc region |
| mAb8 | VH5/VL6 with IgG1 Fc region |
| mAb9 | VH4/VL4 with IgG1 AlaAla mutant Fc region |
| mAb10 | VH4/VL5 with IgG1 AlaAla mutant Fc region |
| mAb11 | VH5/VL4 with IgG1 AlaAla mutant Fc region |
| mAb12 | VH5/VL6 with IgG1 AlaAla mutant Fc region |
| mAb13 | VH4/VL4 with IgG1 N297A mutant Fc region |
| mAb14 | VH4/VL5 with IgG1 N297A mutant Fc region |
| mAb15 | VH5/VL4 with IgG1 N297A mutant Fc region |
| mAb16 | VH5/VL6 with IgG1 N297A mutant Fc region |

Transient Expression and Purification of Human IgG

Cells were transfected with expression vector DNA encoding for heavy and light chains of IgGs mAb1 to mAb16.

The results are shown in FIG. 4. The results revealed that the antibodies produced with IgG4 isotype are produced with a better yield as compared to other isotype, IgG1 and mutant silent IgG1.

Profiling Data Related to mAb1

TABLE 9

Profiling data of mAb1

| Selection Criteria | mAb1 |
|---|---|
| human TfR binding affinity (SPR, $K_D$ nM) | 0,315 nM |
| HL-60 apoptosis induction | 0.2 to 10 µg/ml |
| EC50 in ELISA assay | 0.024 µg/ml |

Remarkably, the antibodies of the invention have $K_D$ affinity and $EC_{50}$ below 10 nM, and even below 1 nM and have better induction of apoptosis as measured in the HL-60 apoptosis assay than A24, therefore being particularly suitable for use as a drug.

Moreover, they possess advantageous developability properties, in particular for production in eukaryotic cell lines and administration to human due to predicted reduced immunogenicity.

The coding sequences encoding the variable regions can be easily transferred in suitable expression vectors and cell lines for generating silent IgG1 antibodies, for example comprising the IgG1 Fc variant containing the L234A L235A mutation, or the IgG1 Fc variant containing the N297A mutation.

Alternatively, the coding sequences encoding the variable regions may also be transferred to expression vectors and cell lines for generating antibodies with high ADCC activity, for example comprising IgG1 Fc wild type, and/or with bisecting GlcNAc or low fucosylation of the glycan at N297 amino acid position.

The invention claimed is:

1. A method for treating a tumor expressing transferrin receptor (TfR) in a human subject in need thereof, comprising administering a therapeutically effective amount of an anti-TfR antibody or protein to said subject, wherein said anti-TfR antibody or protein is an isolated anti-TfR antibody or a protein with an antigen-binding portion of an anti-TfR antibody, comprising:
   (a) a variable heavy chain polypeptide comprising VH of SEQ ID NO:11 and a variable light chain polypeptide comprising VL of SEQ ID NO:13;
   (b) a variable heavy chain polypeptide comprising VH of SEQ ID NO:11 and a variable light chain polypeptide comprising VL of SEQ ID NO:14;
   (c) a variable heavy chain polypeptide comprising VH of SEQ ID NO:11 and a variable light chain polypeptide comprising VL of SEQ ID NO:15;
   (d) a variable heavy chain polypeptide comprising VH of SEQ ID NO:12 and a variable light chain polypeptide comprising VL of SEQ ID NO:13;
   (e) a variable heavy chain polypeptide comprising VH of SEQ ID NO:12 and a variable light chain polypeptide comprising VL of SEQ ID NO:14; or
   (f) a variable heavy chain polypeptide comprising VH of SEQ ID NO:12 and a variable light chain polypeptide comprising VL of SEQ ID NO:15;
   wherein said anti-TfR antibody or protein specifically binds to the TfR of SEQ ID NO:16.

2. The method of claim 1, wherein said tumor a hematologic tumor.

3. The method of claim 1, wherein said tumor is a solid tumor.

\* \* \* \* \*